US009700492B2

(12) United States Patent
Bowman et al.

(10) Patent No.: US 9,700,492 B2
(45) Date of Patent: *Jul. 11, 2017

(54) DENTAL COMPOSITES SYSTEMS AND METHODS OF MAKING THE SAME AND USING SAME

(71) Applicant: THE REGENTS OF THE UNIVERSITY OF COLORADO, A BODY CORPORATE, Denver, CO (US)

(72) Inventors: Christopher N. Bowman, Boulder, CO (US); Weixian Xi, Boulder, CO (US); Shunsuke Chatani, Yokohama (JP); Tao Gong, Superior, CO (US); Devatha P. Nair, Denver, CO (US); Maciej Podgorski, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,809

(22) Filed: Mar. 6, 2015

(65) Prior Publication Data

US 2015/0250687 A1    Sep. 10, 2015

Related U.S. Application Data

(60) Provisional application No. 61/949,709, filed on Mar. 7, 2014.

(51) Int. Cl.
| | | |
|---|---|---|
| *C08F 2/46* | (2006.01) | |
| *C08F 2/50* | (2006.01) | |
| *C08G 61/04* | (2006.01) | |
| *A61K 6/087* | (2006.01) | |
| *C08G 18/73* | (2006.01) | |
| *C08G 18/67* | (2006.01) | |
| *C08G 18/38* | (2006.01) | |
| *A61K 6/00* | (2006.01) | |

(52) U.S. Cl.
CPC ............ *A61K 6/087* (2013.01); *A61K 6/0079* (2013.01); *C08G 18/3876* (2013.01); *C08G 18/677* (2013.01); *C08G 18/73* (2013.01)

(58) Field of Classification Search
CPC .... A61K 6/087; A61K 6/0079; C08G 18/677; C08G 75/20; C08G 18/73; C08G 18/3876
USPC ....................... 522/63, 6, 71, 189, 184, 1, 65
See application file for complete search history.

(56) References Cited

U.S. PATENT DOCUMENTS

| | | | |
|---|---|---|---|
| 6,365,072 B1 | 4/2002 | Katoot et al. | |
| 8,192,673 B2 | 6/2012 | Bowman et al. | |
| 2003/0017424 A1 | 1/2003 | Park et al. | |
| 2006/0263301 A1 | 11/2006 | Vernon et al. | |
| 2008/0021166 A1 | 1/2008 | Tong et al. | |
| 2008/0085946 A1 | 4/2008 | Mather et al. | |
| 2008/0269460 A1 | 10/2008 | Bowman et al. | |
| 2010/0311861 A1 | 12/2010 | Clapper et al. | |
| 2013/0090443 A1* | 4/2013 | Musa | A01N 25/24 526/263 |
| 2014/0271601 A1 | 9/2014 | Aimetti et al. | |
| 2015/0031782 A1* | 1/2015 | Bowman | C08F 220/18 522/33 |

FOREIGN PATENT DOCUMENTS

| | | |
|---|---|---|
| WO | WO2009/132070 A2 | 10/2009 |
| WO | WO2012061702 A1 | 5/2012 |

OTHER PUBLICATIONS

Chatani et al, Temporal Control of Thiol-Click Chemistry, Sep. 20, 2013, Chemistry of Materials, 25, 3897-3901.*
Suzuki et al, Synthesis of amorphous copoly(thioether sulfone)s with high refractive indices and high Abbe numbers, Sep. 12, 2009, European Polymer Journal, 46, 34-41.*
Suzuki et al, Synthesis and characterization of High Refractive Index and High Abbe's number poly(thioether sulfone)s based on tricyclo[5.2.1.02,6]decane Moiety, Apr. 13, 2012, macromolecules, 45, 3402-3408.*
Chatani et al, Relative reactivfity and selectivity of vinyl sulfones and acrylates towaqrds the thiol-michael addition reaction and polymerization, Nov. 19, 2012, Polym. Chem., 4, 1048-1055.*
Jo et al, Biomimetic PEG hydrogels crosslinked with minimal plasmin-sensitive tri-amino acid peptides, Aug. 21, 2009, Journal of Biomedical Materials Research Part A, 870-877.*
Chatani et al, Temporal Control of Thiol-Click chemistry, Sep. 20, 2013, Chem. Mater. 2013, 25, 3897-3901.*
Missirlis et al, Combined Effects of PEG hydrogel Elasticity and Cell-Adhesive Coating on Fibroblast Adhesion and Persistent Migration, Nov. 25, 2013, Biomacromolecules, 15, 195-205.*
Chan, J.W. et al., "Nucleophile-Initiated Thiol-Michael Reactions: Effect of Organocatalyst, Thiol, and Ene," Macromolecules, 2010, vol. 43, pp. 6381-6388.

(Continued)

*Primary Examiner* — Jessica E Whiteley
(74) *Attorney, Agent, or Firm* — Saul Ewing LLP; Kathryn Doyle; Domingos J. Silva

(57) ABSTRACT

The invention includes a composition comprising a vinyl sulfone monomer, a thiol monomer, and optionally an isocyanate monomer. The invention further includes a composition comprising a composition comprising the tetra(2-mercapto)silane (SiTSH) monomer and at least one selected from the group consisting of (a) a Michael acceptor, optionally an isocyanate monomer, and optionally at least one catalyst selected from the group consisting of a base, nucleophile, photolabile base, photolabile nucleophile, and mixtures thereof; (b) an ene monomer, and optionally a polymerization photoinitiator. In certain embodiments, once the composition is polymerized, the polymerized system is suitable for use as a dental composite system. In other embodiments, the polymerized system is stable to acidic and basic conditions. In yet other embodiments, the polymerized system forms microparticles. The invention further includes a method of generating a dental polymeric material.

26 Claims, 20 Drawing Sheets

(56) References Cited

OTHER PUBLICATIONS

Chatani, S. et al., "Reactivity and Selectivity of Vinyl Sulfones Towards the Thiol-Michael Addition Reaction and Their Implementation to Two-Stage Reactive Polymer Systems," Polymeric Materials Science and Engineering, ACS Abstract, ACS National Meeting and Exposition, New Orleans, Louisiana, 2013.
Chatani, S. et al., "Relative Reactivity and Selectivity of Vinyl Sulfones and Acrylates Towards the Thiol-Michael Addition Reaction and Polymerization," Polym. Chem., 2013, vol. 4, pp. 1048-1055.

\* cited by examiner

Fig. 1A
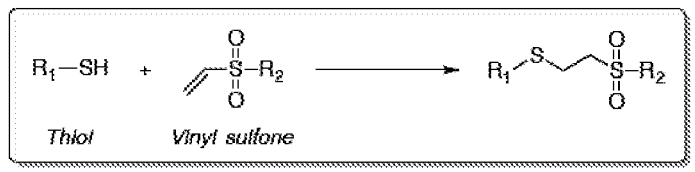
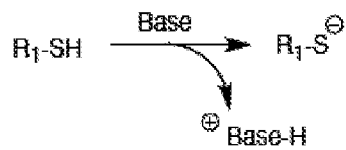
Fig. 1B
Nucleophile-catalyzed Mechanism
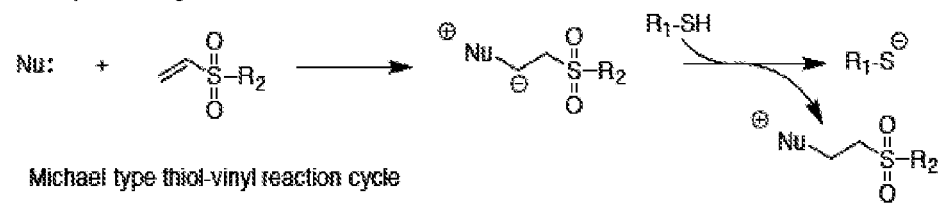
Michael type thiol-vinyl reaction cycle
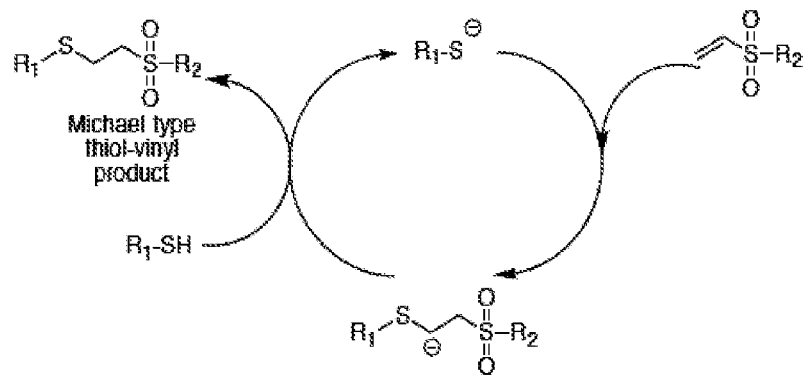
Fig. 1C
Radical-mediated Mechanism
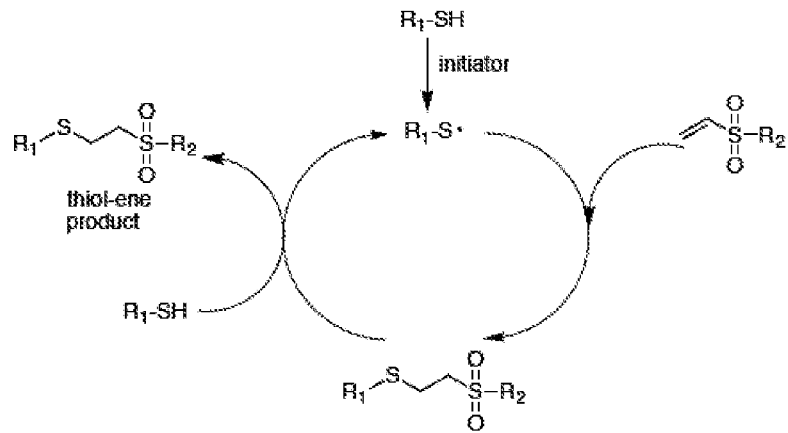

Tri-thiol    TATATO    Tri-vinyl sulfone excess base

Fig. 8
Thiols - two-step reaction: radical thiol-ene and acetyl deprotection (hydrolysis)
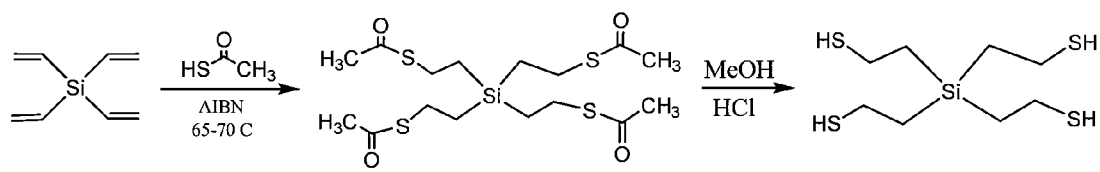
Vinyl sulfones - four-step reaction:
1 – radical thiol-ene, 2 – OH substitution with Cl,
3 – thioether oxidation, 4 – HCl elimination
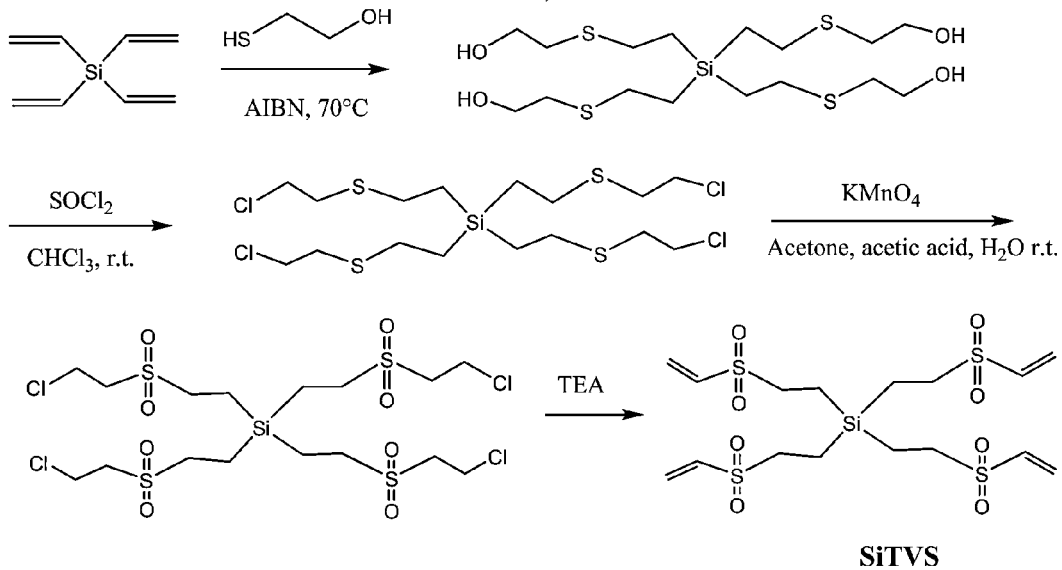
SiTVS Fig. 9
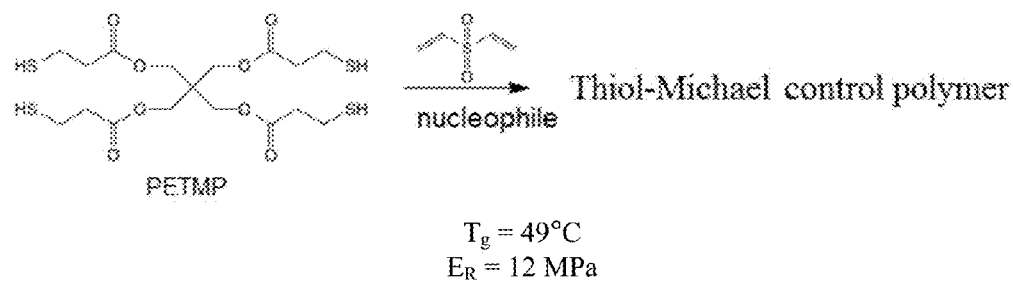
$T_g = 49°C$
$E_R = 12$ MPa
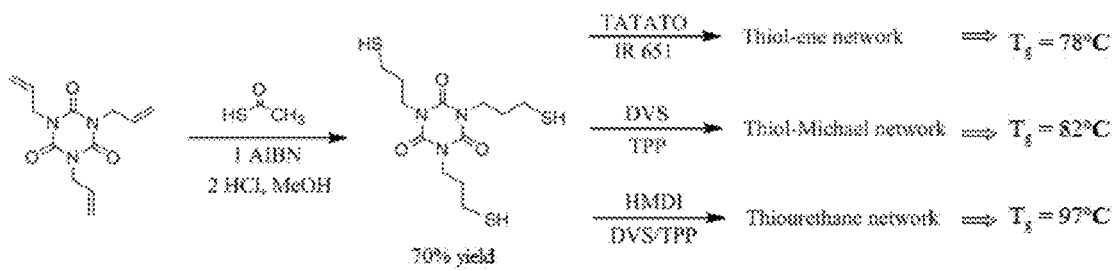
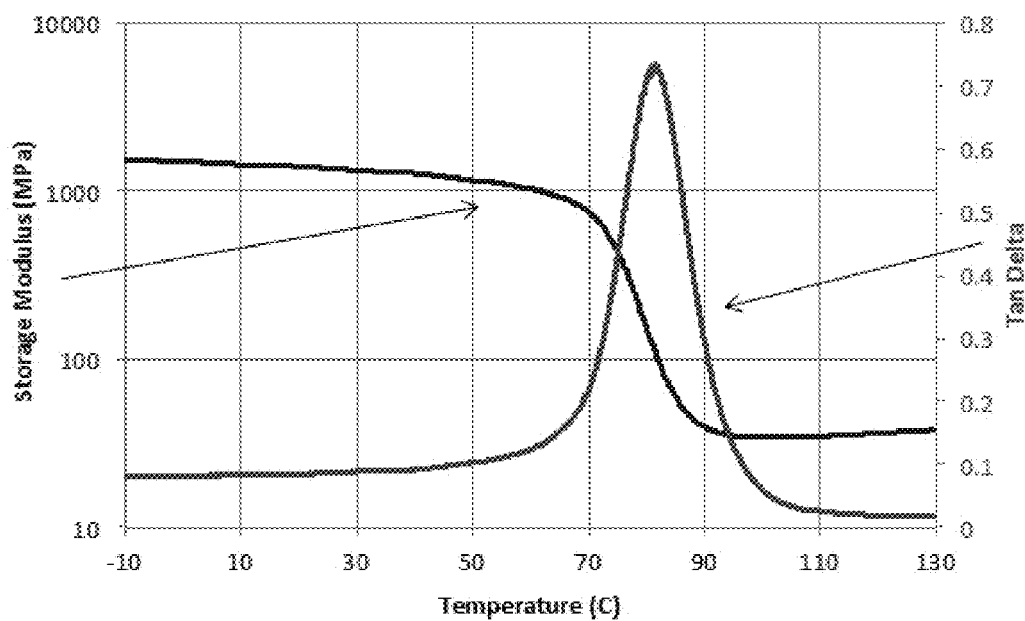
Tetrathiol/DVS stoichiometric system Fig. 10
| Polymer System | Glass transition (°C) | Toughness (J/mm$^3$) |
| --- | --- | --- |
| BisGMA/TEGDMA | 169 | 0.001 |
| PETMP/DVS | 50 | 0.004 |
| PETMP/HMDI/DVS | 59 | 0.003 |
| Polymer System | Water sorption (μg/mm$^3$) | Water solubility (μg/mm$^3$) |
| --- | --- | --- |
| BisGMA/TEGDMA | 36.9 ± 1.1 | 2.9 ± 1.2 |
| PETMP/DVS | 23.7 ± 1.9 | 0.5 ± 0.2 |
| PETMP/HMDI/DVS (1M / 1M / 1M) | 27.6 ± 0.8 | 1.8 ± 0.8 |
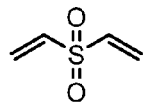
Divinyl sulfone (DVS)
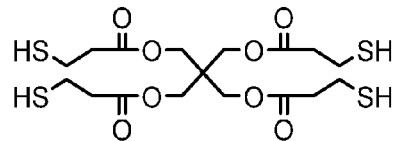
Pentaerythritol tetrakis(3-mercaptopropionate) (PETMP)
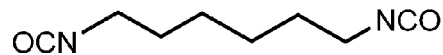
Hexamethylene diisocyanate (HMDI)

Initiator: 1.5 wt % TEMPO

Dental compositions:

1M SiTSH
1M DCPDVS  } $T_g$ = 86 C; $E_R$ = 6-7 MPa
1M DVS

2M SiTSH
3M DCPDVS  } $T_g$ = 99 C; $E_R$ = 6 MPa
1M DVS

2M SiTSH
3M DCPDVS  } $T_g$ = 99 C; $E_R$ = 6-7 MPa
1M HMDI

1M PETMP
1M DCPDVS  } $T_g$ = 56 C; $E_R$ = 6-7 MPa
1M DVS

1M SiTVS
2M DCPDSH  } $T_g$ = 112 C; $E_R$ = 20 MPa
2M SiTSH
4M DVS

Fig. 13

Dimethylphenylphosphine
tetraphenylborate salt
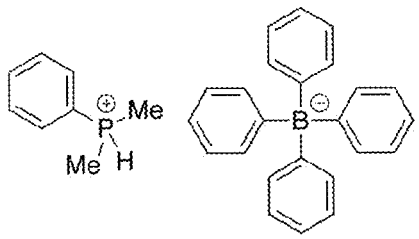

P

ETMP/DVS stoichiometric mixture
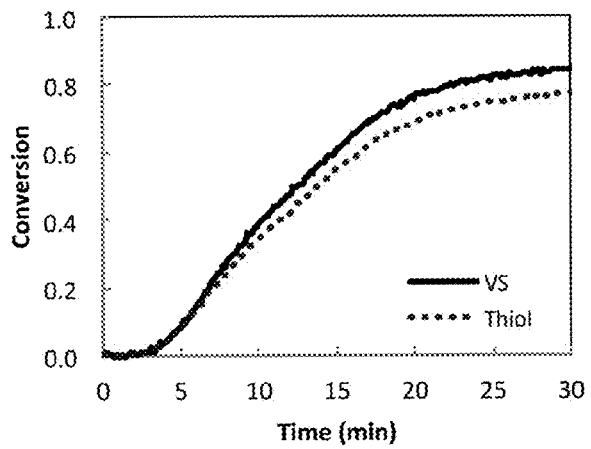

ITX/DMPP photobase/radical inhibitor = 1.0/2.0/1.0 (wt%)

Triazabicyclodecene tetraphenylborate
salt (TBDphotobase)          PETM
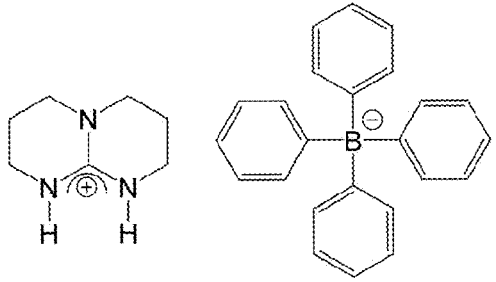

P/DVS stoichiometric mixture
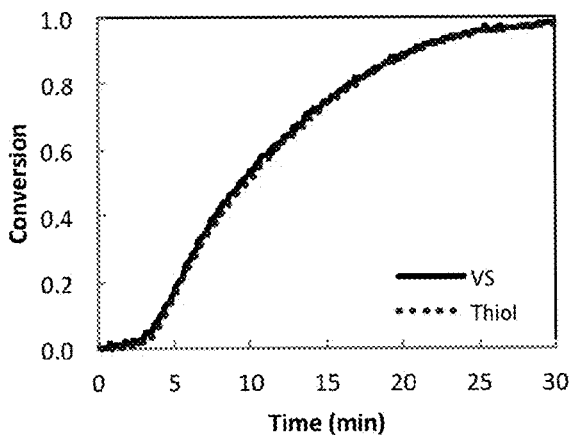

ITX/TBD photobase/radical Inhibitor = 1.0/2.0/1.0(wt%)

Samples irradiated with 15-30 mW/cm$^2$ light (400-500nm filter)
ITX - Isopropyl thioxanthone (sensitizer)

DENTAL COMPOSITES SYSTEMS AND METHODS OF MAKING THE SAME AND USING SAME

CROSS-REFERENCE TO RELATED APPLICATIONS

The present application claims priority under 35 U.S.C. §119(e) to U.S. Provisional Application No. 61/949,709, filed Mar. 7, 2014, which is hereby incorporated by reference in its entirety herein.

STATEMENT REGARDING FEDERALLY SPONSORED RESEARCH OR DEVELOPMENT

This invention was made with government support under grant number CHE1214109 awarded by the National Science Foundation. The government has certain rights in the invention.

BACKGROUND OF THE INVENTION

More than 100 million dental restorations are performed each year with more than half of those presently being filled using composite restorative materials. Despite this scale of usage and implementation, the composite restorative is often not a lifelong restoration of either function or appearance. Secondary caries, mechanical failure and various other failure mechanisms are responsible for reducing the useful lifetime of many restorations. Further, the bioavailability and degradation of monomers that are extracted from conventional composites has been implicated in several adverse phenomena, including reduced immune function, changes to the microbial distribution in the oral environment, and the acceleration of growth of bacteria involved in the evolution of biofilms and additional secondary cavities that result in reduced service lifetimes.

Currently, most commercial photocurable dental restorative resins are based on dimethacrylates and the reaction mechanism is through chain-growth free radical polymerization. Existing dimethacrylate systems are popular for fillings and other dental prostheses because of their esthetic merit and "cure-on-command" feature. These formulations have resulted in significant advancements in the field of dentistry. Such dental restorative materials are often mixed with 45 to 85% by weight (wt %) silanized filler compounds such as barium, strontium, zirconia silicate and/or amorphous silica to match the color and opacity to a particular use or tooth.

Although easy to use, these dimethacrylate systems have several drawbacks and there are a number of properties of the resin chemistry that, if improved upon, would increase the performance, longevity and biocompatibility of composite restorations (Sakaguchi et al., 2005, Dent. Mat. 21:43-46; Dauvillier et al., 2001, J. Biomed. Mat. Res. 58(1):16-26, 2001; Dauvillier et al., 2000, J. Dent. Res. 79(3):818-823; Yourtee et al., 1997, In Vitro Tox. 10:245-251). The most significant shortcomings of methacrylate-based resins are high volumetric shrinkage (Ferracane, 2005, Dent. Mat. 21:36-42), high polymerization stress (Braga et al., 2005, Dent. Mat. 21:962-970; Lu et al., 2005, Dent. Mat., 21(12): 1129-1136; Braga and Ferracane, 2002, J. Den.1 Res. 81:114-118) and low functional group conversion (Darmani and Al-Hiyasat, 2006, Dent. Mat. 22:353-358; Sasaki et al., 2005, J. Mat. Sci.: Mat. Med. 16:297-300; Pulgar et al., 2000, Envir. Health Persp. 108:21-27). The chain growth polymerization mechanism results in long chains and therefore early gelation which contributes to both volume shrinkage and shrinkage stress. The current systems typically only reach a final double bond conversion of 55-75%, which not only contributes to the insufficient wear resistance and mechanical properties, but also jeopardizes the biocompatibility of the composites due to the leachable unreacted monomers. Additionally, the residual monomer left in the restoration after curing is extractable and reactive due to its ester functionalities (inherent to methacrylates), and may leach out of the restoration and into the body, with unknown consequences (Sasaki et al., 2005, J. Mat. Sci.: Mat. Med. 16:297-300; Pulgar et al., 2000, Envir. Health Persp. 108: 21-27). There is concern that residual monomers may cause allergic reactions and sensitization in patients (Theilig et al., 2000, J. Biomed. Mat. Res. 53(6):632-639). There is also reason to believe that release of the most common reactive diluent, triethylene glycol dimethacrylate (TEGDMA), may also contribute to local and systemic adverse effects by dental composites (Hansel et al., 1998, J. Dent. Res. 77(1): 60-67; Englemann et al., 2001, J. Dent. Res. 80(3):869-875; Schweikl and Schmalz, 1999, Mut. Res.-Gen. Toxic. Envir. Mutag. 438:71-78; Darmani and Al-Hiyasat, 2006, Dent. Mat. 22:353-358).

Upon polymerization, shrinkage stresses transferred to the tooth can cause deformation of the cusp or enamel microcracks (Davidson and Feilzer, 1997, J. Dent. Res. 25:435-440; Suliman et al., 1993, J. Dent. Res. 72(11):1532-1536; Suliman et al., 1993, J. Dent. Res. 9(1):6-10), and stress at the tooth-composite interface may cause adhesive failure, initiation of microleakage and recurrent caries. In addition, significant increases in volumetric shrinkage and shrinkage stress are experienced when the double bond conversion is increased to reduce the leachable monomer (Lu et al., 2004, J. Biomed. Mat. Res. Part B—Applied Biomat. 71B:206-213). This trade-off of conversion and shrinkage has been an inherent problem with composite restorative materials since their inception.

Nucleophilic reactions of thiols to several functional groups such as electron deficient vinyls (i.e., thiol-Michael addition reaction), isocyanates and epoxides are known to proceed extremely efficiently under mild conditions, with no by-products at room temperature, minimal amounts of catalysts like a base, high functional group tolerance and high conversions, and thus widely considered as "click" reaction (Hoyle et al., 2010, Chem. Soc. Rev. 39:1355-1387; Hoyle & Bowman, 2010, Angew. Chem. Int. Ed. 49:1540-1573; Lowe, 2010, Polym. Chem. 1:17-36). The thiol-X reaction family has been used in organic synthesis, polymer formation, and materials modification in recent decades (Hoyle et al., 2004, J. Polym. Sci., Part A: Polym. Chem. 42:5301-5338; Hoyle et al., 2010, Chem. Soc. Rev. 39:1355-1387; Hoyle & Bowman, 2010, Angew. Chem., Int. Ed. 49:1540-1573; Lowe, 2010, Polym. Chem. 1:17-36) Given that the versatile thiol-click chemistry can be used to synthesize highly functional materials under relatively *facile* reaction conditions, various thiol-vinyl reaction qualify as highly efficient click reactions as used in applications that range from complex dendrimer synthesis (Killops et al., 2008, J. Am. Chem. Soc. 130:5062-50645), convergent synthesis of star polymers (Chan et al., 2008, Chem. Commun. 40:4959-4961), functional biodegradable lactides (Nuttelman et al., 2008, Prog. Polym. Sci. 33:167-179) to surface modifications of films (Khire et al., 2007, Macromolecules 40:5669-5677) and nanoparticles (Khire et al., 2008, J. Polym. Sci., Part A: Polym. Chem. 46:6896-69069). One of the most powerful aspects of the thiol-vinyl reaction family is that it can be mediated by various species such as radicals (i.e., the classical thiol-ene reaction), acids, bases, nucleophiles and highly polar solvents. Each of these reaction pathways exhibits some or all of the characteristic advantages of the thiol-vinyl reaction.

A base or nucleophile mediated thiol reaction, often referred to as the thiol-Michael addition reaction, has attracted great interest for its high reactivity with relatively low amount of catalysts and its orthogonality to radical mediated reactions. Among several catalysts that are used for the thiol-Michael addition reaction, nucleophiles such as organophosphines (Chan et al., 2010, Macromolecules 43:6381-6388) and nucleophilic tertiary amines (Xi et al., 2012, ACS Macro Lett. 1:811-814) are known to be efficient catalysts for the thiol-Michael addition reaction. An activated vinyl, also referred to as an electron deficient vinyl, is suitable for thiol-Michael addition reactions since it accelerates the nucleophilic attack of a thiolate anion on a vinyl (Mather et al., 2006, Prog. Polym. Sci. 31:487-531). Carbonyl conjugated vinyls, such as acrylates and maleimides are well known as activated vinyls for Michael addition. Vinyl sulfone, a sulfone conjugated vinyl, is a functional group that has a highly electron deficient vinyl and has been used extensively as a textile dye since the 1950's (U.S. Pat. No. 2,657,205). The vinyl sulfone group is highly reactive towards the hydroxyl groups of the cellulose present in textile fibers under alkaline conditions. Additionally, the thiol-Michael addition product of vinyl sulfone forms a very stable thioether sulfone bond (Mather et al., 2006, Prog. Polym. Sci. 31:487-531; Morales-Sanfrutos et al., 2010, Org. Biomol. Chem. 8:667-675), while the counterparts of acrylates and maleimides contain relatively labile thioether ester or succinimide bonds (Schoenmakers et al., 2004, J. Controlled Release 95:291-300; Rydholm et al., 2007, Acta Biomater. 3:449-455).

There is a need in the art to develop novel monomer systems that afford useful composites systems once polymerized. Such composite systems should have superior chemical and physical properties, allowing for their use in challenging applications, such as dental restorations. The present invention fulfills these needs.

BRIEF SUMMARY OF THE INVENTION

The invention includes a composition comprising a vinyl sulfone monomer, a thiol monomer, and optionally an isocyanate monomer, wherein once polymerized the composition is suitable for use as a dental composite system.

The invention further includes a composition comprising the tetra(2-mercapto)silane (SiTSH) monomer and at least one selected from the group consisting of (a) a Michael acceptor monomer, optionally an isocyanate monomer, and optionally at least one catalyst selected from the group consisting of a base, nucleophile, photolabile base, photolabile nucleophile, and mixtures thereof; and (b) an ene monomer, and optionally a polymerization photoinitiator.

The invention further includes a method of generating a dental polymeric material, the method comprising promoting polymerization of a composition comprising: a vinyl sulfone monomer; a thiol monomer; at least one catalyst selected from the group consisting of a base, a nucleophile, a photolabile base, a photolabile nucleophile, and mixtures thereof; and optionally an isocyanate monomer; thereby generating the dental polymeric material.

The invention further includes a method of photoinducing a thiol-Michael addition reaction, the method comprising photo-irradiation a composition comprising a thiol monomer, a Michael acceptor monomer, and at least one catalyst selected from the group consisting of a photolabile base, a photolabile nucleophile, and mixtures thereof.

The invention further includes a method of generating a polymeric material, the method comprising polymerizing at least partially a composition comprising the tetra(2-mercapto)silane (SiTSH) monomer and at least one selected from the group consisting of (a) a Michael acceptor, optionally an isocyanate monomer, and optionally at least one catalyst; (b) an ene monomer, and optionally a polymerization photoinitiator.

In certain embodiments, the monomers in the composition are unpolymerized. In other embodiments, the monomers in the composition are at least partially polymerized. In yet other embodiments, the monomers in the composition are unpolymerized or at least partially polymerized.

In certain embodiments, the Michael acceptor monomer comprises a (meth)acrylate, maleamide, or vinyl sulfone. In other embodiments, photoinduction of the thiol-Michael addition reaction promotes at least partial polymerization of the monomers.

In certain embodiments, the composition further comprises at least one catalyst selected from the group consisting of a base, a nucleophile, a photolabile base, a photolabile nucleophile, and mixtures thereof. In other embodiments, the at least one catalyst is selected from the group consisting of a base, a nucleophile, a photolabile base, a photolabile nucleophile, and mixtures thereof. In yet other embodiments, the photolabile base or photolabile nucleophile comprises a protective group selected from the group consisting of:

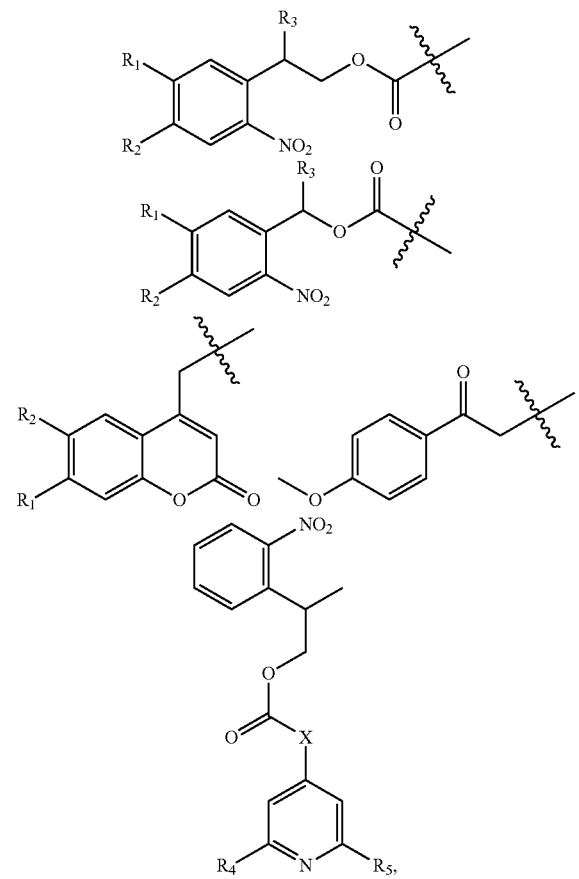

wherein: each occurrence of $R_1$ and $R_2$ is independently H or $OCH_3$, each occurrence of $R_3$ is independently H, $CH_3$, C(=O)OH or C(=O)OCH₃, X is NH or O, and each occurrence of R₄ and R₅ is independently H or CH₃.

In certain embodiments, the catalyst comprises a tertiary amine, wherein each substituent on the tertiary amine or phosphine is independently alkyl, substituted alkyl, aryl or substituted aryl. In other embodiments, the catalyst comprises at least one compound selected from the group consisting of:

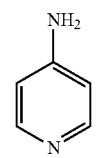
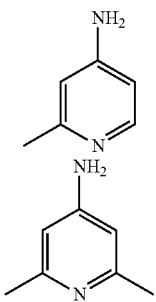
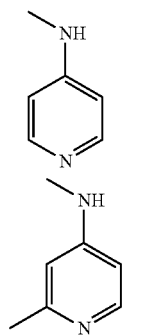
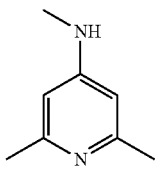
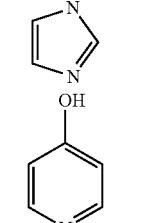
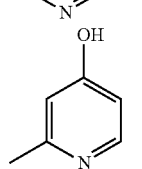
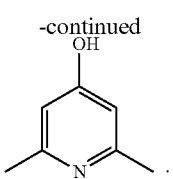

In certain embodiments, the composition undergoes at least partial polymerization when the catalyst is photo-cleaved. In other embodiments, the isocyanate monomer is absent and (i) the thiol equivalent concentration is approximately equal to vinyl sulfone equivalent concentration, or (ii) the thiol equivalent and vinyl sulfone equivalent concentrations are selected such that, upon polymerization of the composition, at least 80% polymerization of the thiol or vinyl sulfone monomers is observed. In yet other embodiments, the isocyanate monomer is absent; and wherein (i) the thiol equivalent concentration is approximately equal to the Michael acceptor equivalent concentration, or (ii) the thiol equivalent and Michael acceptor equivalent concentrations are selected such that, upon polymerization of the composition, at least 80% polymerization of the thiol or Michael acceptor monomers is observed.

In certain embodiments, the isocyanate is present and selected from the group consisting of a monofunctional isocyanate, a polyfunctional isocyanate, and mixtures thereof. In yet other embodiments, (i) the thiol equivalent concentration is approximately equal to the sum of the vinyl sulfone equivalent and the isocyanate equivalent concentrations, or (ii) the thiol equivalent, vinyl sulfone equivalent and isocyanate equivalent concentrations are selected such that, upon polymerization of the composition, at least 80% polymerization of the thiol monomer or vinyl sulfone monomer is observed. In yet other embodiments, (i) the thiol equivalent concentration is approximately equal to the sum of the Michael acceptor equivalent and the isocyanate equivalent concentrations, or (ii) the thiol equivalent, Michael acceptor equivalent and isocyanate equivalent concentrations are selected such that, upon polymerization of the composition, at least 80% polymerization of the thiol monomer or Michael acceptor monomer is observed.

In certain embodiments, the composition further comprises a filler. In other embodiments, the filler comprises a thiol- or a vinyl sulfone-functionalized particle.

In certain embodiments, the vinyl sulfone monomer is at least one selected from the group consisting of ethyl vinyl sulfone, divinyl sulfone,

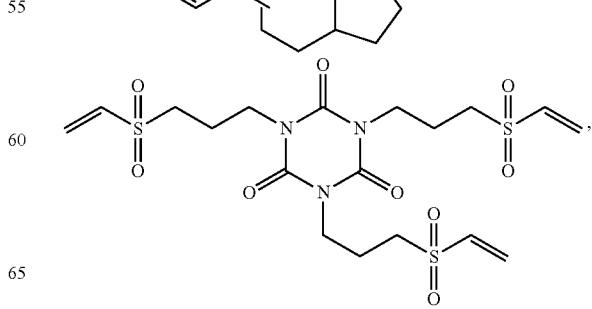

-continued

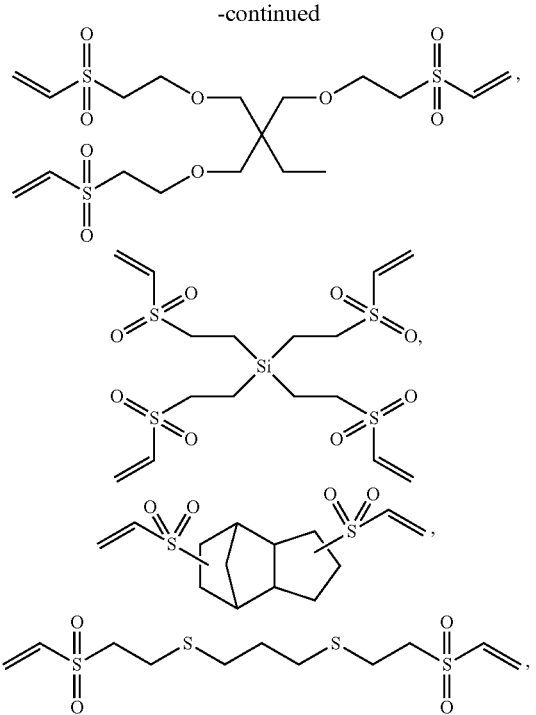

and any combinations thereof.

In certain embodiments, the thiol monomer is at least one selected from the group consisting of 2,5-dimercaptomethyl-1,4-dithiane, 2,3-dimercapto-1-propanol, 2-mercapto-ethyl-sulfide, 2,3-(dimercaptoethylthio)-1-mercaptopropane, 1,2,3-trimercaptopropane, ethylene glycol bis(thioglycolate), ethylene glycol bis(3-mercaptopropionate), pentaerythritol tetra(3-mercaptopropionate), trimethylolpropane tris(3-mercaptopropionate), pentaerythritol tetra(2-mercaptoacetate), trimethylolpropane tris(2-mercaptoacetate), 1,6-hexanedithiol, 1,2-benzenedithiol, 1,3-benzenedithiol, isophorone diurethane thiol,

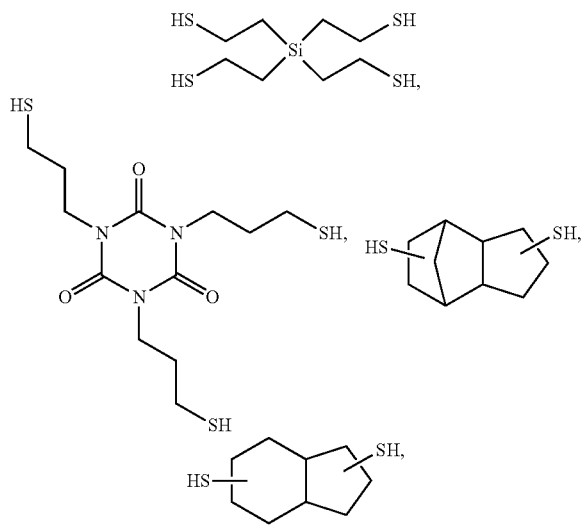

and any combinations thereof. In other embodiments, the composition is essentially free of any other thiol monomer apart from SiTSH.

In certain embodiments, the composition further comprises a polymerization accelerator or inhibitor. In other embodiments, the thiol monomer is monofunctional, difunctional, trifunctional, tetrafunctional, pentafunctional or hexafunctional, as to the thiol group. In yet other embodiments, the vinyl sulfone monomer is monofunctional, difunctional, trifunctional, tetrafunctional, pentafunctional or hexafunctional, as to the vinyl sulfone group. In yet other embodiments, promoting polymerization comprises photoirradiating the composition. In yet other embodiments, the at least partially polymerized composition is stable to acidic or basic conditions.

In certain embodiments, the monomers are at least partially polymerized by step-growth dispersion click chemistry to form microspheres. In other embodiments, the microspheres have an average diameter within a range selected from the group consisting of: from 0.5 µm to 100 µm, from 1 µm to 50 µm, from 0.5 µm to 1 µm; and from 1 µm to 10 µm. In yet other embodiments, the microspheres are near-monodisperse or monodisperse. In yet other embodiments, the micropheres have a glass transition temperature (Tg) in the range of −50° C. to 100° C. or a Tg in the range of −24° C. to 16° C.

BRIEF DESCRIPTION OF THE DRAWINGS

The following detailed description of certain embodiments of the invention will be better understood when read in conjunction with the appended drawings. For the purpose of illustrating the invention, the drawings embodiments illustrate specific embodiments of the invention. It should be understood, however, that the invention is not limited to the precise arrangements and instrumentalities of the embodiments shown in the drawings.

FIGS. 1A-1C are schematic illustrations of the thiol-vinyl sulfone reaction. (FIG. 1A) Base and (FIG. 1B) nucleophile catalyzed pathways for generating the thiolate anion, which then initiates the Michael type thiol-vinyl reaction cycle. The radical mediated (FIG. 1C) thiol-vinyl sulfone step-growth reaction mechanism is also presented, here involving alternating chain transfer and propagation steps that lead to the thioether product. Independent of the mechanistic pathway, the result in all cases is an addition product that does not necessarily possess ester or other unstable moieties, such as those prevalent in traditional methacrylate systems.

In FIG. 3B, the thiol and vinyl sulfones monomers that can be synthesized using a triazine core such as that of TATATO is described and FIG. 3C outlines a synthetic method to design multifunction vinyl sulfones systems.

FIG. 7A illustrates photolabile groups contemplated within the invention. FIG. 7B illustrates a synthetic route for a series of NPPOC-protected pyridines that have the ability to release the amine upon exposure to light. FIG. 7B (bottom) further illustrates typical photolysis reaction of NPPOC-hexylamine. FIG. 7C illustrates the UV/Vis spectra of NPPOC-hexylamine (0.05 mM) before and after photolysis using 320-390 nm irradiation in MeOH. FIG. 7D illustrates the thiol converison as a function of time, as measured by FTIR, for a stoichimetric mixture of butyl thiol glycolate and methyl acrylate using 5% NPPOC-hexylamine under continuous (filled square), 4 min (open triangle), 2 min 320-390 nm irradiation (filled triangle), and no irradiation (open circle) as well as no NPPOC-hexylamine under continuous irradiation (filled circle). FIGS. 7E-7F illustrate the tan δ and elastic modulus plots vs temperature for networks formed from a stoichiometric mixture of PETMA (FIG. 7E), PETMP (FIG. 7F) and bisphenol A ethoxy diacrylate. FIG. 7G illustrates structures of nitrogen centered nucleophiles used in catalyst design for the photoinduced thiol-Michael addition.

FIG. 8 illustrates synthetic routes to multifunctional thiols and vinyl sulfones.

FIG. 9 illustrates polymerization experiments within the invention.

FIG. 10 illustrates mechanical properties and water sorption of polymer composite of the invention. Top table: Mechanical analysis of thiol-vinyl sulfone/thiocarbamate polymer networks indicate that, in spite of the lower $T_g$ and crosslinking density of the control methacrylate system, the thiol-vinyl sulfone systems were comparable to the control system with the PETMP/DVS system having 3 times the toughness of the dimethacrylate control. Bottom table: Swelling tests show that the thiol-vinyl sulfone and thiocarbamate/vinyl sulfone samples exhibit lower water sorption and solubility than the control BisGMA/TEGDMA.

FIG. 13 illustrates photobase and photonucleophile generators for thiol-Michael crosslinking polymerization reactions.

FIGS. 14A-14C illustrate real time kinetic profiles (C═C conversions) for: (FIG. 14A) radical thiol-ene reaction between SiTSH and PETMP with TTT; (FIG. 14B) thiol-Michael reaction between SiTSH and PETMP with DVS and (FIG. 14C) thiol-Michael reaction between SiTSH and PETMP with TMPTA. Radical thiol-ene processes reached in both cases high conversions after 4 min of irradiation with visible light (400-500 nm) of 50 mW/cm². The alkyl thiol reacted with lower initial rates. The thiol-Michael reaction was initiated thermally with 1 wt % TEMPO, and longer reaction times were required to reach high conversions.

(FIG. 15B) SiTSH/DVS and PETMP/DVS thiol-vinyl sulfone networks and (FIG. 15C) SiTSH/TMPTA and PETMP/TMPTE thiol-acrylate networks. The more ester functionalities present in the network, the softer the material. SiTSH-based polymers exhibit exclusively higher $T_g$'s than PETMP-based polymers.

DETAILED DESCRIPTION OF THE INVENTION

Figure 2:
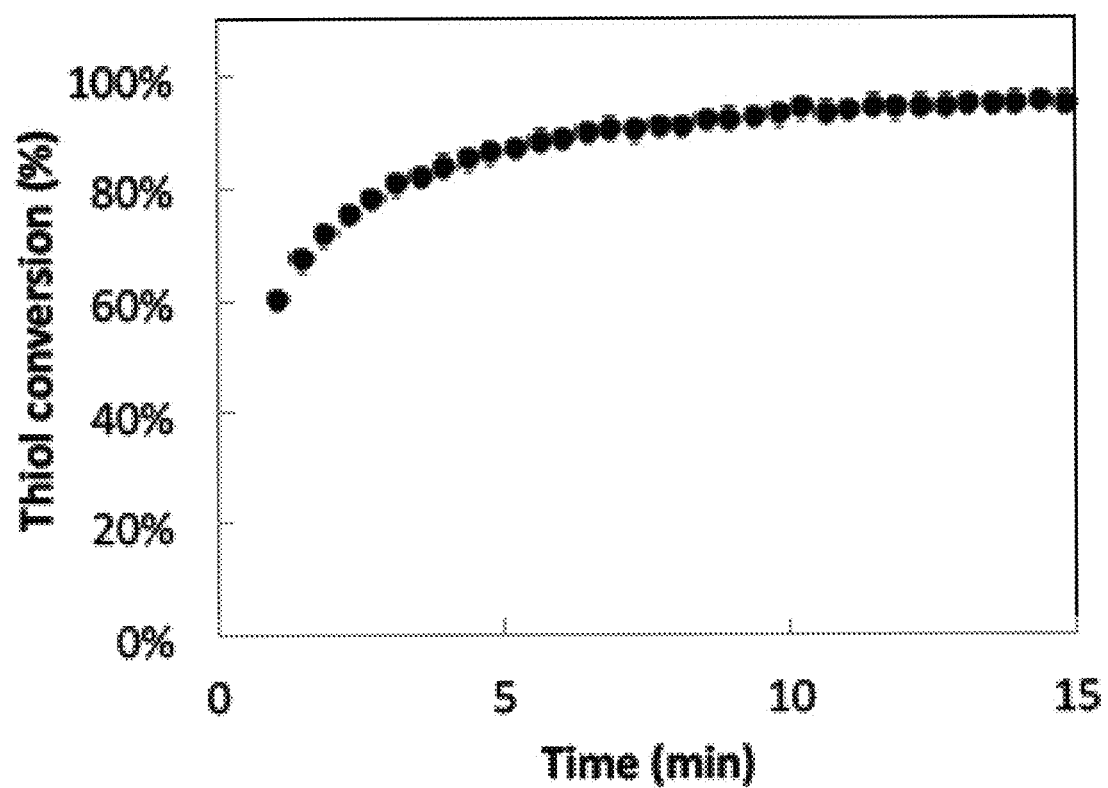
FIG. 2 is a graph illustrating thiol conversion as a function of time plots for model thiol-vinyl sulfone system with 1-hexanethiol and ethyl vinyl sulfone catalysed by 0.05 wt % methyldiphenylphosphine.

The invention relates to the unexpected discovery of novel monomer systems that afford useful composite systems once polymerized. In one aspect, the composite systems of the invention have superior chemical and physical properties, allowing for their use in applications such as dental restoration. In certain embodiments, the composite systems of the invention are characterized by one or more of the following: reduced biological and/or chemical degradation; improved physical and mechanical properties over currently available composite materials; improved interfacial interaction with fillers, ensuring compatibility and improved mechanical resistance; and improved interaction with current adhesive systems, allowing for strong covalent interactions with the adhesive.

The reaction further relates to novel photolabile catalysts for thiol-Michael coupling reaction. In certain embodiments, the catalysts of the invention allow for spatiotemporal control of the thiol-Michael coupling reaction. In other embodiments, upon photo-irradiation, the photolabile catalysts are converted to thiol-Michael coupling reaction catalysts.

In certain embodiments, a series of thiol-Michael and radical thiol-ene network polymers were successfully prepared from ester-free as well as ester-containing monomer formulations. Polymerization reaction rates, dynamic mechanical analysis, and solvent resistance experiments were performed and compared between compositions with varied ester loading. The incorporation of ester-free alkyl thiol, vinyl sulfone and allylic monomers significantly improved the mechanical properties when compared with commercial, mercaptopropionate-based thiol-ene or thiol-Michael networks. For polymers with no hydrolytically degradable esters, glass transition temperatures ($T_g$'s) as high as 100° C. were achieved. Solvent resistance tests demonstrated extraordinary stability of ester-free formulations over PETMP-based polymers, especially in concentrated basic solutions. Kinetic analysis showed that glassy step-growth polymers are readily formed at ambient conditions with conversions reaching 80% and higher.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in organic chemistry, and polymer chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, ±5%, ±1%, or ±0.1% from the specified value, as such variations are appropriate to perform the disclosed methods.

As used herein, the term "acrylate equivalent concentration" for an acrylate monomer in a sample corresponds to the concentration of reactive acrylate groups in the sample related to the acrylate monomer. In a non-limiting example, the acrylate equivalent concentration of an acrylate monomer in a solution corresponds to the product of the average number of reactive acrylate groups in an acrylate monomer and the average concentration of the acrylate monomer in the solution.

As used herein, the term "acrylate monomer" corresponds to a compound having a discrete chemical formula and comprising at least one acrylate group (exemplified as —C($R^1$)=C($R^2$)—C(=O)—), wherein $R^1$ and $R^2$ are independently hydrogen or alkyl), or a reactive oligomer or reactive polymer or pre-polymer having at least one acrylate group In a non-limiting embodiment, the term "acrylate" encompass a methacrylate, wherein $R^2$ is methyl.

The term "aliphatic" or "aliphatic group" as used herein means a straight-chain or branched hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl" and "alkoxy," used alone or as part of a larger moiety include both straight and branched carbon chains. The terms "alkenyl" and "alkynyl" used alone or as part of a larger moiety shall include both straight and branched carbon chains.

The term "aralkyl" refers to an alkyl group substituted by an aryl. The term "aralkoxy" refers to an alkoxy group. The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring".

As used herein, the terms "comprising," "including," "containing" and "characterized by" are exchangeable, inclusive, open-ended and does not exclude additional, unrecited elements or method steps. Any recitation herein of the term "comprising," particularly in a description of components of a composition or in a description of elements of a device, is understood to encompass those compositions and methods consisting essentially of and consisting of the recited components or elements.

As used herein, "consisting essentially of" does not exclude materials or steps that do not materially affect the basic and novel characteristics of the claim.

As used herein, "consisting of" excludes any element, step, or ingredient not specified in the claim element.

As used herein, the term "curable" as applied to a material refers to a material comprising at least one functional group that may undergo polymerization. The curable material may be non-polymerized (i.e., non-cured material), or may be submitted to polymerization conditions (such as chemical reagents or physical conditions) that induce polymerization of at least a fraction of the at least one polymerizable functional group (i.e., partially or fully cured material). In certain embodiments, polymerization or crosslinking of the curable material results in about 100% consumption of the at least one functional group (i.e., fully cured). In other embodiments, polymerization or crosslinking of the curable material results in less than about 100% consumption of the at least one functional group (i.e., partially cured).

As used herein, the term "DVS" refers to divinyl sulfone.

As used herein, the term "electromagnetic radiation" includes radiation of one or more frequencies encompassed within the electromagnetic spectrum. Non-limiting examples of electromagnetic radiation comprise gamma radiation, X-ray radiation, UV radiation, visible radiation, infrared radiation, microwave radiation, radio waves, and electron beam (e-beam) radiation. In one aspect, electromagnetic radiation comprises ultraviolet radiation (wavelength from about 10 nm to about 400 nm), visible radiation (wavelength from about 400 nm to about 750 nm) or infrared radiation (radiation wavelength from about 750 nm to about 300,000 nm). Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In certain embodiments, the UV light source emits light between about 350 nm and about 400 nm. In some embodiments, the UV light source emits light between about 400 nm and about 500 nm.

Monomers having "-ene" or vinyl functional groups suitable for embodiments of the present invention include any monomer having one or more functional vinyl groups, i.e., reacting "C=C" or "C≡C" groups. The ene monomer can be selected from one or more compounds having vinyl functional groups. Vinyl functional groups can be selected from, for example, vinyl sulfone, vinyl ether, vinyl ester, allyl ether, norbornene, diene, propenyl, alkene, alkyne, N-vinyl amide, unsaturated ester, N-substituted maleimides, and styrene moieties. Examples of ene monomers include triallyl-1,3,5-triazine-2,4,6-trione (TATATO); Triethyleneglycol divinyl ether (TEGDVE); Trimethylolpropane diallyl ether; 1,6-heptadiyne; 1,7-octadiyne; and Dodecyl vinyl ether (DDVE) and norbornene monomers. In one specific embodiment, the ene monomer is selected from triallyl-1,3,5-triazine-2,4,6-trione (TATATO), 1-octanethiol 1,6-hexanedithiol triethyleneglycol divinyl ether (TEGDVE), and dodecyl vinyl ether (DDVE). In another specific embodiment, the ene monomer is triallyl-1,3,5-triazine-2,4,6-(1H,3H,5H)-trione (TATATO).

As used herein, the term "EVS" refers to ethyl vinyl sulfone.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen.

As used herein, the term "HT" refers to hexanethiol.

As used herein, the term "Irgacure 819" refers to bis(2, 4,6-trimethylbenzoyl)-phenylphosphineoxide*BPO).

As used herein, the term "isocyanate equivalent concentration" for an isocyanate monomer in a sample corresponds to the concentration of reactive isocyanate groups in the sample related to the isocyanate monomer. In a non-limiting example, the isocyanate equivalent concentration of an isocyanate monomer in a solution corresponds to the product of the average number of reactive isocyanate groups in an isocyanate monomer and the average concentration of the isocyanate monomer in the solution.

As used herein, the term "isocyanate monomer" corresponds to a compound having a discrete chemical formula and comprising at least one isocyanate group (—N=C=O), or a reactive oligomer or reactive polymer or pre-polymer having at least one isocyanate group. Suitable isocyanate monomers have one or more functional isocyanate groups and may be of any molecular weight. Non-limiting examples of isocyanates useful within the invention include monofunctional isocyanates (wherein the isocyanate group is covalently linked to a moiety such as alkyl, cycloalkyl, aryl or heteroaryl, wherein the moiety is optionally further substituted) or polyfunctional isocyanates, such as but not limited to hexamethylene diisocyanate, 4,4'-methylenebis(phenyl isocyanate), 1,4-phenylene diisocyanate, 1,3-phenylene diisocyanate, isophorone diisocyanate, toluene 2,4-diisocyanate, cyclohexylene diisocyanate, and mixtures thereof.

As used herein, the term "instructional material" includes a publication, a recording, a diagram, or any other medium of expression that may be used to communicate the usefulness of the compositions and/or methods of the invention. In some instances, the instructional material may be part of a kit useful for generating a polymeric composite. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

The terms "mercapto" or "thiol" refer to an —SH substituent, or are used to designate a compound having an —SH substituent.

As used herein, the term "monofunctional" as applied to a group in a molecule indicates the molecule comprises a single occurrence of the group.

The term "monomer" refers to any discreet chemical compound of any molecular weight.

As used herein, the term "orthogonal," as applied to the conditions required to run at least two distinct chemical reactions, indicates that the conditions used to perform one of the chemical reactions do not significantly affect the ability to perform the subsequent other(s) chemical reaction(s). In a non-limiting example, reactions R1 and R2 may be performed in a system, wherein R1 is run first and R2 is run second; reactions R1 and R2 are performed under "orthogonal" conditions if reaction R1 may be performed in the system under conditions that do not affect the ability to subsequently perform reaction R2 in the system.

As used herein, the term "PETMP" refers to pentaerythritol tetra(3-mercaptopropionate.

As used herein, the term "polyfunctional" as applied to a group in a molecule indicates the molecule comprises one or more occurrences of the group. The term "polyfunctional" comprises difunctional (2 occurrences of the group), trifunctional (3 occurrences of the group), tetrafunctional (4 occurrences of the group), pentafunctional (5 occurrences of the group), hexafunctional (6 occurrences of the group), and so on.

As used herein, the term "polymer" refers to a molecule composed of repeating structural units typically connected by covalent chemical bonds. The term "polymer" is also meant to include the terms copolymer and oligomers. In certain embodiments, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In certain embodiments, polymerization or crosslinking of at least one functional group results in about 100% consumption of the at least one functional group. In other embodiments, polymerization or crosslinking of at least one functional group results in less than about 100% consumption of the at least one functional group.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "reactive" as applied to thiol, alcohol, isocyanate, vinyl, acrylate or ene groups indicate that these groups, when submitted to appropriate conditions, may take part in the reaction in question.

As used herein, the term "thiol equivalent concentration" for a thiol monomer in a sample corresponds to the concentration of reactive thiol groups in the sample related to the thiol monomer. In a non-limiting example, the thiol equivalent concentration of a thiol monomer in a solution corresponds to the product of the average number of reactive thiol groups in a thiol monomer and the average concentration of the thiol monomer in the solution.

As used herein, the term "SiTSH" refers to tetra(2-mercaptoethyl)silane, or a salt or solvate thereof.

As used herein, the term "TEA" refers to trimethylamine, or a salt thereof.

As used herein, the term "TEMPO" refers to 2,2,6,6-tetramethylpiperidine 1-oxyl.

As used herein, the term "thiol monomer" corresponds to a compound having a discrete chemical formula and comprising at least a sulfhydryl or thiol group (—SH), or a reactive oligomer or reactive polymer or pre-polymer having at least one thiol group. Suitable thiol monomers have one or more functional thiol groups and may be of any molecular weight. In certain embodiments, the thiol monomer may be selected from one or more of aliphatic thiols, thiol glycolate esters, thiol propionate esters. Examples of thiol bearing monomers include: pentaerythritol tetra(3-mercaptopropionate) (PETMP); 1-octanethiol; Butyl 3-mercaptopropionate; 2,4,6-trioxo-1,3,5-triazina-trig (triethyl-tris(3-mercapto propionate); 1,6-hexanedithiol; 2,5-dimercaptomethyl-1,4-dithiane, pentaerythritol tetramercaptoacetate, trimethylolpropane trimercaptoacetate, 2,3-dimercapto-1-propanol, 2-mercaptoethylsulfide, 2,3-(dimercaptoethylthio)-1-mercaptopropane, 1,2,3-trimercaptopropane, toluenedithiol, xylylenedithiol, 1,8-octanedithiol, 1-hexanethiol (Sigma-Aldrich, Milwaukee, Wis.); and trimethylolpropane tris(3-mercaptopropionate), and glycol dimercaptopropionate (Evans Chemetics LP, Iselin, N.J.).

As used herein, the term "TMPTA" refers to trimethylolpropane triacrylate.

As used herein, the term "TTT" refers to triallyl-1,3,5-triazine-2,4,6-(1H,3H,5H)-trione.

As used herein, the term "vinyl sulfone concentration" for a vinyl sulfone monomer in a sample corresponds to the concentration of reactive vinyl sulfone groups in the sample related to the vinyl sulfone monomer. In a non-limiting example, the vinyl sulfone equivalent concentration of a vinyl sulfone monomer in a solution corresponds to the product of the average number of reactive vinyl sulfone groups in a vinyl sulfone monomer and the average concentration of the vinyl sulfone monomer in the solution.

As used herein, the term "vinyl sulfone monomer" corresponds to a compound having a discrete chemical formula and comprising at least one vinyl sulfone group (exemplified as $-C(R^1)=C(R^2)-S(=O)_2-$), wherein $R^1$ and $R^2$ are independently hydrogen or alkyl), or a reactive oligomer or reactive polymer or pre-polymer having at least one vinyl sulfone group.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Disclosure:

The present invention relates to novel monomer systems that can be polymerized into useful composite systems. In one aspect, the composite systems of the invention have superior chemical and physical properties, allowing for their use in challenging applications, such as dental restoration.

In certain embodiments, the monomer systems and/or composite systems of the invention are essentially free of ester groups. In other embodiments, the monomer systems of the invention can be polymerized with high conversion of the polymerizable functional groups. In yet other embodiments, the monomer systems of the invention can be polymerized either by radical-mediated and nucleophile-mediated mechanisms to enable both rapid-term and long-term reactions. In yet other embodiments, the monomer systems of the invention can be polymerized via a step growth mechanism that lowers the shrinkage and also significantly increases the gel point conversion of the system, thus reducing the polymer stress. In yet other embodiments, the composite systems of the invention can include thiocarbamates, which impart certain desirable mechanical and toughening behaviors of urethane-based materials and are compatible with the monomer systems and composite systems of the invention.

In certain aspects, the thiol-vinyl sulfone reaction is useful within the invention. This reaction is particularly useful and innovative in developing novel dental materials. The reaction is biocompatible, and the thioether-sulfone product is not hydrolytically or enzymatically cleavable, making it an alternative to methacrylates. Further, the ability to catalyze this reaction using either radicals and/or nucleophiles enables a unique combination of short-term and long-term reaction capabilities that further increase conversion and reduce extractables. Further, composite systems based on thiol-vinyl sulfone monomers can include thiocarbamates, wherein sulfur replaces an oxygen from a conventional urethane. These thiocarbamates have certain similar advantageous mechanical attributes to urethanes (i.e., carbamates) and are stable in biomedical applications. FIG. 1 illustrates the thiol-vinyl sulfone reaction with radical, nucleophile and base-mediated pathways. When multifunctional thiols and vinyl sulfones are used, a highly crosslinked polymer network is efficiently formed.

In certain embodiments, the step growth nature of the thiol-vinyl sulfone reaction is such that in these systems the shrinkage per functional group is low and the gel point conversion is high. Because a composite's post-gelation shrinkage is the primary adverse stress contributor, the thiol-vinyl sulfone polymerization systems experience much lower stress than comparable polymerization systems.

In certain aspects, the composite systems of the invention improve upon the biological, chemical reaction and mechanical behavior of traditional methacrylate based composite systems. The ability of thiol-vinyl sulfone polymers to attain high functional group conversions in a short amount of time, along with the absence of ester bonds and the complete elimination of enzymatically reactive functional groups from the polymer, render these systems superior choices as dental materials. In certain embodiments, thiocarbamates can be incorporated into the thiol-vinyl sulfone polymers, imparting certain desirable mechanical and toughening behaviors characteristic of urethane-based methacrylate materials and thus resulting in a glassy, robust, tough, stable polymer network.

The present invention further includes fillers, bonding agents and coupling agents that may be used with the monomer systems of the invention. In certain embodiments, use of biocompatible thiol and vinyl monomers with rigid backbones and side chains within the invention allow for optimal reaction behavior and mechanical properties for a dental resin system. In other embodiments, functionalized fillers are incorporated into the composite systems of the invention to optimize their performance as dental composite systems.

In certain embodiments, the inclusion of fillers in the compositions of the invention improve their mechanical performance and reduces shrinkage, stress and moisture uptake. Fillers generally enhance the hardness of the materials while also imparting increased wear resistance and reducing polymerization shrinkage. Most importantly, the nature, type, size distribution, and surface modification of the filler significantly contribute to the integration of the filler within the resin as necessary to improve the overall mechanical strength and function of the dental composite over its life cycle.

The present invention further includes novel photolabile compounds that, once photoactivated, allow for the photoinduction of thiol-Michael additions. As discussed elsewhere herein, the thiol-Michael reaction is generally catalyzed through either a base- and nucleophile-pathway. However, there are no reported light-mediated methods to control this reaction. Such methods would have a significant impact in several material fabrication strategies. In particular, the utility of the nucleophile- or base-catalyzed thiol-vinyl "click" reaction as a dental composite curing reaction would be enhanced with development of a non-toxic, efficient photocatalyst for thiol-Michael addition.

In certain embodiments, the photoactivated thiol-Michael reaction is fast and efficient, and yet leaves little potential for extended dark reactions that would reduce the extractable level further. In contrast, the nature of the base/nucleophile reaction is such that the catalyst exists for the life of the restoration once formed-enabling significant reaction in the minutes or hours after exposure that will be critical in eliminating the small amount of residual, extractable monomers and preventing further degradation. As demonstrated herein, designing and developing a dual photolabile catalyst for the thiol-vinyl sulfone Michael addition reaction and the thiol-vinyl sulfone radical reaction mechanisms facilitates the efficient spatio-temporal control that is necessary for a dental composite resin to function efficiently and achieve quantitative conversions.

In certain embodiments, the photolabile catalyst comprises a photolabile protecting group connected with a primary amine, which is recognized as a catalyst for thiol-Michael addition reaction. In other embodiments, the photolabile catalyst comprises a photolabile protecting group connected with a nitrogen-containing nucleophile, such as 4-amino pyridine, which is also recognized as a catalyst for thiol-vinyl sulfone Michael addition. In yet other embodiments, the photolabile groups contemplated within the invention include 2-nitrobenzyl, benzoin, phenacyl, and coumarin, for example.

Compositions:

The invention includes a composition comprising a vinyl sulfone monomer, a thiol monomer, and optionally an isocyanate monomer, wherein once polymerized the composition is suitable for use as a dental composite system.

The invention further includes a composition comprising the tetra(2-mercapto)silane (SiTSH) monomer and at least one selected from the group consisting of (a) a Michael acceptor monomer, optionally an isocyanate monomer, and optionally at least one catalyst selected from the group consisting of a base, nucleophile, photolabile base, photolabile nucleophile, and mixtures thereof and (b) an ene monomer, and optionally a polymerization photoinitiator. In certain embodiments, the composition is essentially free of any other thiol monomer apart from SiTSH.

In certain embodiments, the monomers in the composition are unpolymerized. In other embodiments, the monomers in the composition are at least partially polymerized.

Figure 7A:
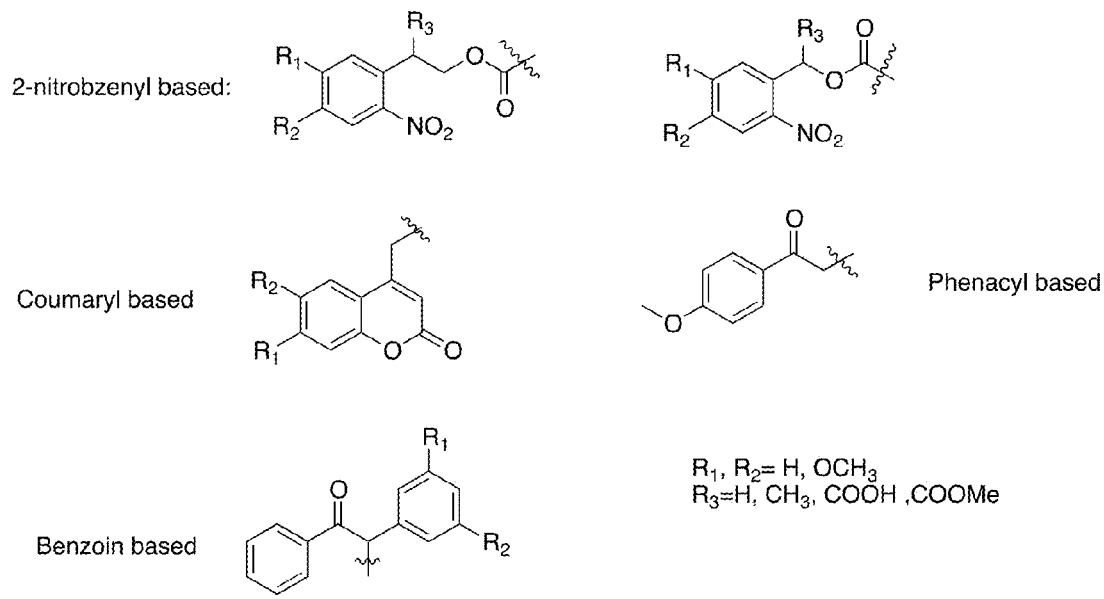
FIGS. 7A-7G, illustrates embodiments relating to photolabile catalysts for the thiol-Michael additions.
Figure 7B:
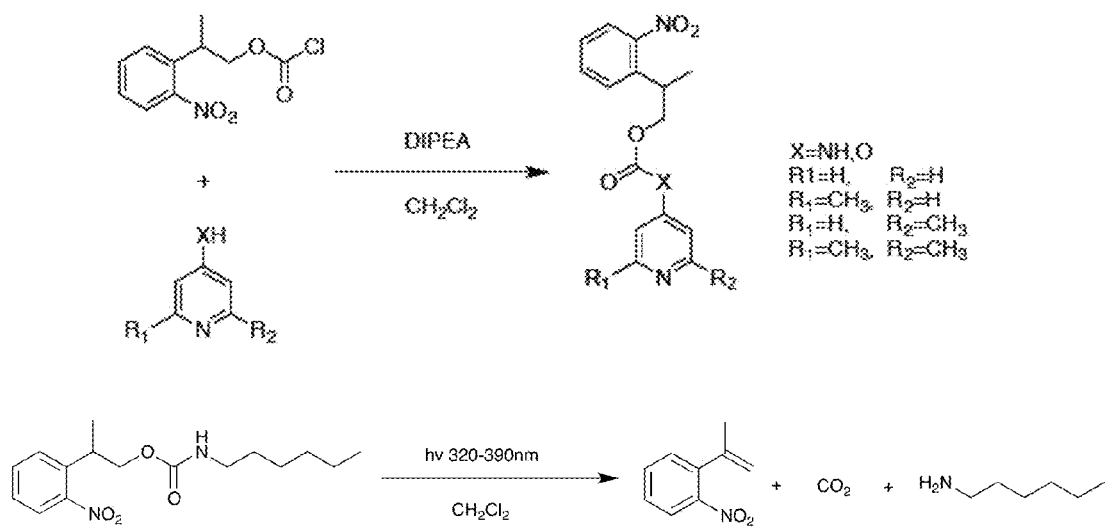
Figure 7C:
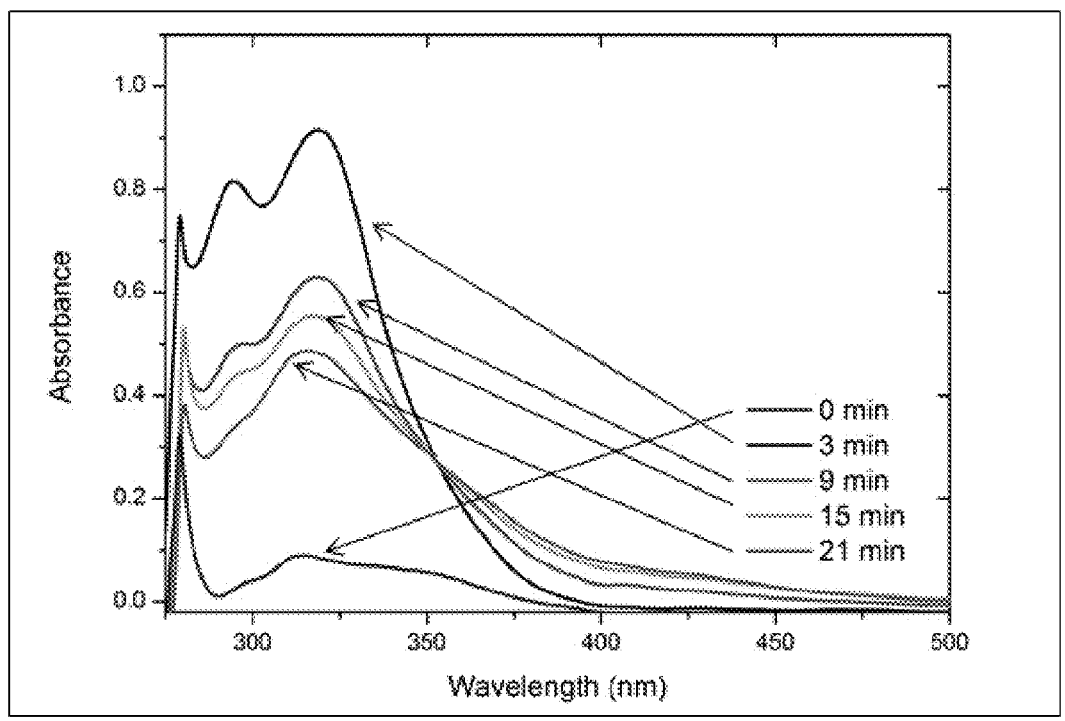

In certain embodiments, the composition further comprises at least one catalyst selected from the group consisting of a base, a nucleophile, a photolabile base, a photolabile nucleophile, and mixtures thereof. In other embodiments, the photolabile base or photolabile nucleophile comprises a protective group as illustrated in FIGS. 7A-7B. In yet other embodiments, the catalyst comprises a tertiary amine, wherein each substituent on the tertiary amine or phosphine is independently alkyl, substituted alkyl, aryl or substituted aryl. In yet other embodiments, the catalyst comprises a compound as illustrated in FIG. 7G.

In certain embodiments, the composition undergoes at least partial polymerization when the catalyst is photo-cleaved.

In certain embodiments, the isocyanate monomer is absent and the thiol equivalent concentration is approximately equal to vinyl sulfone equivalent concentration. In other embodiments, the isocyanate monomer is absent and the thiol equivalent and vinyl sulfone equivalent concentrations are selected such that, upon polymerization of the composition, at least 80% polymerization of the thiol or vinyl sulfone monomers is observed.

In certain embodiments, the isocyanate is present and selected from the group consisting of a monofunctional isocyanate, a polyfunctional isocyanate, and mixtures thereof. In other embodiments, the thiol equivalent concentration is approximately equal to the sum of the vinyl sulfone equivalent and the isocyanate equivalent concentrations. In yet other embodiments, the thiol equivalent, vinyl sulfone equivalent and isocyanate equivalent concentrations are selected such that, upon polymerization of the composition, at least 80% polymerization of the thiol monomer or vinyl sulfone monomer is observed.

In certain embodiments, the composition further comprises a filler. In other embodiments, the filler comprises a thiol- or a vinyl sulfone-functionalized particle. In certain embodiments, the vinyl sulfone monomer is at least one selected from the group consisting of ethyl vinyl sulfone, divinyl sulfone,

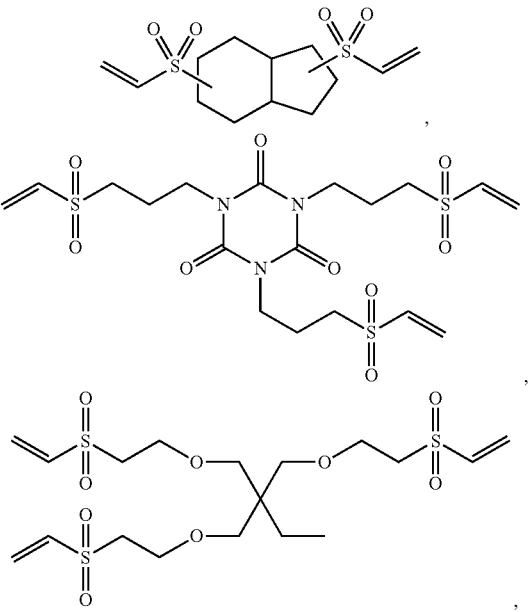

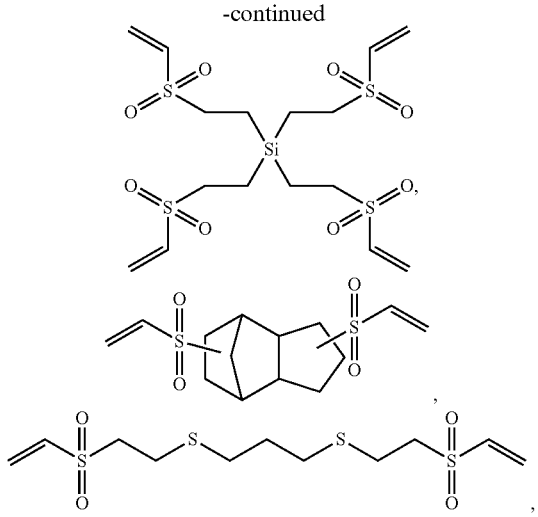

and any combinations thereof.

In certain embodiments, the thiol monomer is at least one selected from the group consisting of 2,5-dimercaptomethyl-1,4-dithiane, 2,3-dimercapto-1-propanol, 2-mercapto-ethyl-sulfide, 2,3-(dimercaptoethylthio)-1-mercaptopropane, 1,2,3-trimercaptopropane, ethylene glycol bis(thioglycolate), ethylene glycol bis(3-mercaptopropionate), pentaerythritol tetra(3-mercaptopropionate), trimethylolpropane tris(3-mercaptopropionate), pentaerythritol tetra(2-mercaptoacetate), trimethylolpropane tris(2-mercaptoacetate), 1,6-hexanedithiol, 1,2-benzenedithiol, 1,3-benzenedithiol, isophorone diurethane thiol,

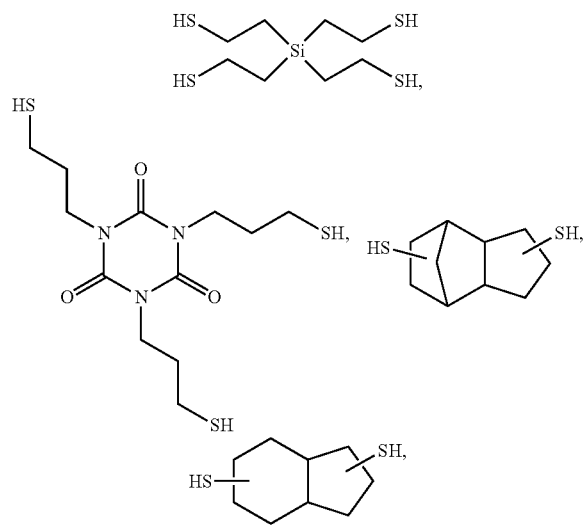

and any combinations thereof.

In certain embodiments, the composition further comprises a polymerization accelerator or inhibitor.

In certain embodiments, the thiol monomer is monofunctional, difunctional, trifunctional, tetrafunctional, pentafunctional or hexafunctional, as to the thiol group.

In certain embodiments, the vinyl sulfone monomer is monofunctional, difunctional, trifunctional, tetrafunctional, pentafunctional or hexafunctional, as to the vinyl sulfone group.

In certain embodiments, the monomers are at least partially polymerized by step-growth dispersion click chemistry to form microspheres. In other embodiments, the microspheres have an average diameter within a range selected from the group consisting of: from 0.5 µm to 100 µm, from 1 µm to 50 µm, from 0.5 µm to 1 µm; and from 1 µm to 10 µm. In yet other embodiments, the microspheres are near-monodisperse or monodisperse. In yet other embodiments, the micropheres have a glass transition temperature (Tg) in the range of −50° C. to 100° C. or a Tg in the range of −24° C. to 16° C.

In certain embodiments, the resin further comprises a polymerization photoinitiator. In other embodiments, a photoinitiator responsive to visible light is employed. In yet other embodiments, the polymerization photoinitiator is selected from the group consisting of 2,2-dimethoxy-1,2-diphenylethan-1-one, bis(2,4,6-trimethylbenzoyl)-phenyl-phosphineoxide, 1-hydroxycyclohexyl benzophenone, trimethyl-benzoyl-diphenyl-phosphine-oxide, and combinations thereof. In yet other embodiments, the photoinitiator is a bisacyl phosphine oxide (BAPO). In yet other embodiments, the BAPO photoinitiator is phenyl bis(2,4,6-trimethyl benzoyl)phosphine oxide (Irgacure 819, Ciba). In yet other embodiments, the photoinitiator is a metallocene initiator. In yet other embodiments, the metallocene initiator is Bis(eta 5-2,4-cyclopentadien-1-yl) Bis[2,6-difluoro-3-(1H-pyrrol-1-yl)phenyl]titanium (Irgacure 784, Ciba). In yet other embodiments, if photopolymerization using visible light is desired, camphorquinone (CQ) may be used as an initiator, in combination with an accelerator, such as, for example, ethyl 4-dimethylaminobenzoate (EDAB). Alternatively, if ultraviolet (UV) photopolymerization is desired, then an appropriate UV light activated photoinitiator may be employed. For example, the photoinitiator can be selected from an alpha-hydroxyketone, such as 1-hydroxy-cyclohexylphenylketone (Irgacure 184, Ciba); a benzyldimethyl-ketal, such as 2,2-dimethoxy-2-phenylacetophenone (DMPA, e.g. Irgacure 651, Ciba), or a number of other commercially available photoinitiators may be used as an initiator. Photoinitiators can be used in amounts ranging from about 0.01 to about 5 weight percent (wt %). In one specific embodiment, 0.25 wt % (2,4,6-trimethyl benzoyl) phosphine oxide (Irgacure 819) is used as the photoinitiator. In another specific embodiment, 0.3 wt % CQ is used as an initiator for visible light experiments, along with 0.8 wt % ethyl 4-(dimethylamino)benzoate (commonly known as EDMAB or EDAB). In another specific embodiment, 0.2 wt % DMPA is used as an initiator for UV polymerization.

In certain embodiments, the free radical initiated photopolymerization is photoinitiated by any light wavelength range within the ultraviolet (about 200 to about 400 nm) and/or visible light spectrum (about 380 to about 780 nm). The choice of the wavelength range can be determined by the photoinitiator employed. In certain embodiments, a full spectrum light source, e.g. a quartz-halogen xenon bulb, may be utilized for photopolymerization. In other embodiments, a wavelength range of about 320 to about 500 nm is employed for photopolymerization.

In certain embodiments, one or more accelerators are utilized in the photopolymerization. Amine accelerators may be used as polymerization accelerators, as well as other accelerators. Polymerization accelerators suitable for use are the various organic tertiary amines well known in the art. In visible light curable compositions, the tertiary amines are generally acrylate derivatives such as dimethylaminoethyl methacrylate and, particularly, diethylaminoethyl methacrylate (DEAEMA), EDAB and the like, in an amount of about 0.05 to about 0.5 wt %. The tertiary amines are generally aromatic tertiary amines, such as tertiary aromatic amines such as EDAB, 2-[4-(dimethylamino)phenyl]ethanol, N, N-dimethyl-p-toluidine (commonly abbreviated DMPT), bis (hydroxyethyl)-p-toluidine, triethanolamine, and the like. Such accelerators are generally present at about 0.5 to about 4.0 wt % in the polymeric component. In certain embodiments, 0.8 wt % EDAB is used in visible light polymerization.

In certain embodiments, the composition further comprises one or more fillers. In certain embodiments, the filler is used to modulate the viscosity, hydrophilicity and stiffness (rubbery modulus) of the unpolymerized or polymerized composition. Non-limiting examples of fillers include inorganic filler compounds such as barium, ytterbium, strontium, zirconia silicate, amorphous silica. The filler may be silanized and typically presented in the form of particles with a size ranging from 0.01 to 5.0 micrometers. In certain embodiments, the filler is a hydrophobic fumed silica. In other embodiments, the hydrophobic fumed silica filler is composed of nanoparticles or nanoclusters.

In certain embodiments, the fillers comprise thiol functionalized filler particles. In other embodiments, the fillers comprise vinyl sulfone functionalized filler particles. In yet other embodiments, the fillers comprise thiol functionalized filler particles andr vinyl sulfone functionalized filler particles. In yet other embodiments, the fillers comprise thiol functionalized filler particles or vinyl sulfone functionalized filler particles.

A nanoparticle is defined as any particle less than 100 nanometers (nm) in diameter. A nanocluster is an agglomeration of nanoparticles. In certain embodiments, utilization of nanoclusters in a nanosized filler can be exploited to increase the load and improve some mechanical properties. Other suitable fillers are known in the art, and include those that are capable of being covalently bonded to the impression material itself or to a coupling agent that is covalently bonded to both. Examples of suitable filling materials include but are not limited to, barium glass, ytterbium nanoglasses and nanoclusters, fumed silica, silica, silicate glass, quartz, barium silicate, strontium silicate, barium borosilicate, strontium borosilicate, borosilicate, lithium silicate, lithium alumina silicate, amorphous silica, ammoniated or deammoniated calcium phosphate and alumina, zirconia, tin oxide, and titania. Some of the aforementioned inorganic filling materials and methods of preparation thereof are disclosed in U.S. Pat. Nos. 4,544,359 and 4,547, 531; pertinent portions of each of which are incorporated herein by reference. In certain embodiments, the filler is a mixture of barium glass, ytterbium nanoglasses and nanoclusters, and fumed silica. In certain embodiments, the filler is 85 wt % 0.5 micron barium glass, 10 wt % ytterbium 40 nm nanoglass and nanoclusters, 2.5 wt % Aerosil fumed silica, and 2.5 wt % Cabosil fumed silica. In other embodiments, the filler is a mixture of 90% 0.4 μm Schott glass and 10 wt % Aerosol OX-50. The above described filler materials may be combined with the resins of the disclosure to form a dental composite material with high strength along with other beneficial physical and chemical properties.

In certain embodiments, suitable fillers are those having a particle size in the range from about 0.01 to about 5.0 micrometers, mixed with a silicate colloid of about 0.001 to about 0.07 micrometers. The filler may be utilized in the filled resin compositions of the disclosure in the amount of from about 40 wt % to about 90 wt %; about 60 wt % to 85 wt %; or about 70 wt % to about 80 wt % of the total weight of the composition. In one specific embodiment, 72.5 wt % filler is utilized in the filled resin composition. In another specific embodiment, 60 wt % filler is utilized in the filled resin composition.

In other embodiments, the resin composition further comprises a polymerization inhibitor, or stabilizer. Examples of inhibitors include hydroquinone monomethyl ether (MEHQ), aluminum-N-nitrosophenylhydroxylamine, and 2,6-di-tertbutyl-4-methylphenol (BHT). In a specific embodiment, the inhibitor is aluminum-N-nitrosophenylhydroxylamine (Q1301, Wako Pure Chemical, Osaka, Japan). The optional inhibitor may be utilized in the amount of from about 0.001 wt % to about 0.5 wt %, or about 0.01 wt % to about 0.1 wt % of the resin composition. In one specific embodiment, the inhibitor aluminum-N-nitrosophenylhydroxylamine is utilized as 0.035 wt % of the resin. In another specific embodiment, aluminum-N-nitrosophenylhydroxylamine is utilized at 0.075 wt % of the total weight of the filled resin composition.

In certain embodiments, the resin composition further comprises a UV absorber. The UV absorber can be selected from, for example, 5-benzoyl-4-hydroxy-2-methoxy-benzenesulfonic acid, Uvinul® 3000 from BASF Corp., and other various benzophenones, e.g. UV-5411 from American Cyanamid. The UV absorber can be present in from about 0.05 to about 5 wt %; or less than about 0.5 wt % of the weight of the total weight of the filled composition. In one specific embodiment, Uvinul® 3000 is present in 0.10 wt % of the total weight of the filled composition.

Methods:

The invention includes a method of generating a dental polymeric material, the method comprising promoting polymerization of a composition comprising: a vinyl sulfone monomer; a thiol monomer; at least one catalyst selected from the group consisting of a base, a nucleophile, a photolabile base, a photolabile nucleophile, and mixtures thereof; and optionally an isocyanate monomer; thereby generating the dental polymeric material.

The invention further includes a method of generating a polymeric material, the method comprising polymerizing at least partially a composition comprising the tetra(2-mercapto)silane (SiTSH) monomer and at least one selected from the group consisting of (a) a Michael acceptor, optionally an isocyanate monomer, and optionally at least one catalyst; (b) an ene monomer, and optionally a polymerization photoinitiator.

In certain embodiments, promoting polymerization comprises photo-irradiating the composition. In other embodiments, the at least one catalyst is selected from the group consisting of a photolabile base, a photolabile nucleophile, and mixtures thereof.

The invention further includes a method of photoinducing a thiol-Michael addition reaction, the method comprising photo-irradiation a composition comprising a thiol monomer, a Michael acceptor monomer, and at least one catalyst selected from the group consisting of a photolabile base, a photolabile nucleophile, and mixtures thereof.

In certain embodiments, the photolabile base or photolabile nucleophile comprises a protective group as illustrated in FIGS. 7A-7B. In other embodiments, the catalyst comprises a tertiary amine, wherein each substituent on the tertiary amine or phosphine is independently alkyl, substituted alkyl, aryl or substituted aryl. In yet other embodiments, the catalyst comprises a compound as illustrated in FIG. 7G. In yet other embodiments, the Michael acceptor monomer comprises a (meth)acrylate, maleamide, or vinyl sulfone. In yet other embodiments, photoinduction of the thiol-Michael addition reaction promotes at least partial polymerization of the monomers.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Reagents disclosed herein, unless otherwise noted, were purchased from commercial vendors and used as received unless otherwise noted.

Trimethylolpropane triacrylate (TMPTA), triethylamine (TEA) triallyl-1,3,5-triazine-2,4,6-(1H,3H,5H)-trione (TTT), 2,2,6,6-tetramethylpiperidine 1-oxyl (TEMPO) were purchased from Sigma-Aldrich. Divinyl sulfone (DVS) was purchased from Oakwood Chemicals. Irgacure 819 (Bis(2,4,6-trimethylbenzoyl)-phenylphosphineoxide-BPO) was obtained from BASF. Pentaerythritol tetra(3-mercaptopropionate) (PETMP) was donated by Bruno Bock. All chemicals were used as received. Tetra(2-mercaptoethyl)silane (SiTSH) was synthesized according to published procedures (Lundberg et al., 2010, ACS Appl. Mater. Interfaces 2:903-912; Suzuki et al., 2012, Macromolecules 45:3402-3408; Podgórski et al., 2014, ACS Appl. Mater. Interfaces 16:6111-6119).

SiTSH:

The ester-free thiol, tetra(2-mercaptoethyl)silane (SiTSH), was synthesized by a two-step methodology, which starts with a radical thiol-ene step followed by an acetyl deprotection step.

To a flask with tetravinyl silane (10.0 g, 73 mmol), thioacetic acid (28.8 g, 378 mmol) was added slowly in an ice-bath. After addition of azobisisobutylronitrile (AIBN) (0.776 g), the solution was stirred at 65° C. for 36 h. After the thiol-ene reaction was complete, the excess amount of thioacetic acid was distilled in vacuo at 65° C. No further purification was performed on the crude product from the first step. Methanol (50 mL) and hydrochloric acid (20 mL) were added to a flask with the crude product from the first step. The solution was stirred at 60° C. for 12 h. After hydrolysis was completed, the solvent was distilled and the product washed twice with 5 wt. % sodium bicarbonate solutions. Finally the crude product was purified by column chromatography (silica gel, DCM/Hexane 1:2) to yield a colorless liquid. $^1$H-NMR (400 MHz, CDCl$_3$, ppm): δ 2.74-2.53 (m, 2H), 1.60 (t, 1H, J=6.9 Hz), 1.18-1.00 (m, 2H).

Non-Limiting Exemplary Characterization:

Fourier Transform Infrared Spectroscopy (Nicolet 6700 FT-IR) combined with a vertical light source was utilized to measure the real-time conversion during curing. The thiol-ene samples were cured in the FTIR chamber using an irradiation intensity of 50 mW/cm$^2$ (400-500 nm) at the surface of the sample which is monitored by a radiometer (model IL1400A equipped with a GaAsP detector and a quartz diffuser). To couple with various mechanical property measurements, near-IR was utilized to evaluate the functional group conversions in polymerizations of 1 mm (DMA, solvent resistance and kinetic analysis) and/or 0.2 mm (kinetic analysis only) thick samples sandwiched between glass slides separated by appropriate spacers. The first C=C overtone signal at 6160 cm$^{-1}$ was monitored during all real-time kinetic runs. Also, the signal of the thiol group at 2560 cm$^{-1}$ was monitored for some of the samples to confirm a stoichiometric pathway of thiol-Michael reaction. For thermal curing a heating stage was utilized which allows for real-time runs at predetermined temperature. Basically, the sample surrounding temperature was gradually increased in the chamber until the final temperature was achieved. The runs were recorded from the moment the samples were placed in the heating compartment. The final temperature was set to be 90° C.

Solvent resistance tests were performed using disc-shaped specimens (n=3) of the dimensions 1 mm in thickness and 5 mm in diameter. The curing was performed in the IR chamber according to the methodology described elsewhere herein. During the immersion tests the sample weight was recorded on a daily, then weekly, and then monthly basis over the maximum period of three months. 10% aqueous NaOH and 10% aqueous HCl were chosen as the hydrolytic media.

Dynamic mechanical analysis (DMA) is used to measure the viscoelastic properties of polymers (such as glass transition temperature, rubbery storage modulus, tan delta). A DMA Q800 (TA Instruments) was utilized in these measurements. Sample specimens with 1×4×10 mm rectangular dimensions were tested in multifrequency strain mode by applying a sinusoidal stress of 1 Hz frequency with the temperature ramping at 3° C./min. The $T_g$ was determined as the maximum of the tan delta curve. The rubbery moduli were determined in the rubbery region at $T_g+30°$ C. $T_g$ half widths were taken as the half width of the tan delta peak at half maximum values.

The monomer and resin viscosities were measured on a TA instruments ARES rheometer. The liquids were placed between 20 mm glass plates with a gap spacing of 0.4 mm. The reported values were recorded at shearing rate of 63 s$^{-1}$.

Example 1

The thiol-vinyl sulfone Michael addition reaction is a highly efficient reaction that can be catalyzed by either a base (e.g., triethylamine) or a nucleophile (e.g., methyldiphenylphosphine) to yield a polymer with essentially quantitative functional group conversion. This reaction proceeds rapidly through an ideal step growth reaction when catalyzed by radicals and bases/nucleophiles.

A model reaction between 1-hexane thiol (HT) and ethyl vinyl sulfone (EVS) catalyzed by a trace amount of the nucleophile methyldiphenylphosphine (MDPP) led to near-quantitative conversion within the first 15 minutes of the reaction (FIG. 2). Higher concentrations of the MDPP beyond 0.5 wt % catalyst led to quantitative conversion of the thiol-vinyl sulfone before the mixture can even be placed in the FTIR for analysis. The vinyl sulfones were much more reactive under these conditions than acrylate functional groups in both the base-catalyzed pathway and the nucleophilic Michael addition reaction pathway.

To demonstrate the excellent mechanical behavior of these polymers, unfilled thiol-vinyl sulfone polymer samples were formed via the thiol-vinyl "click" reaction mechanism using two distinct compositions to yield polymers composed of tetrafunctional thiol and difunctional vinyl sulfone. Dynamic Mechanical Analysis (DMA) tests were performed to obtain the glass transition temperatures of the unfilled thiol-vinyl sulfone polymers formed from a tetrathiol, pentaerythritol tetra(3-mercaptopropionate) (PETMP), and divinyl sulfone (DVS). Otherwise, a diisocyanate (hexamethyldiisocyanate, HMDI), was first reacted with a portion of the thiols to form thiocarbamate linkages, thereby resulting in an ultimate polymer with increased toughness. These polymers were compared with a 70/30 BisGMA/TEGDMA (2,2-bis[p-(3-methacryloxy-2-hydroxypropoxy)phenyl]propane and triethylene glycol dimethacrylate) copolymer as a representative control of conventional dimethacrylate dental resins. The results for these systems are presented in Table 1.

TABLE 1

Mechanical analysis of thiol-vinyl sulfone/thiocarbamate networks indicates that the thiol-vinyl sulfone systems were at least comparable to the control in tensile tests.

| Polymer System | Glass Transition (° C.) | Toughness (J/mm³) |
|---|---|---|
| BisGMA/TEGDMA | 169* | 0.001 |
| PETMP/DVS | 50 | 0.004 |
| PETMP/HMDI/DVS | 59 | 0.003 |

*glass transition temperature increases during heating associated with measurement due to trapped radicals.

All thiol-sulfone and thiol-sulfone/thiocarbamate copolymers were nucleophile-catalyzed from a stoichiometric thiol-vinyl sulfone mixture, whereas the methacrylate control was obtained by radical photopolymerization. The catalyst for the thiol-vinyl sulfone systems was 0.05 wt % of methyldiphenylphosphine (MDPP). As a result of the thiol and vinyl structures used here, the glass transition temperatures of the thiol-vinyl sulfone systems were predictably lower compared to the control dimethacrylate. However, in spite of the lower $T_g$, the thiol-vinyl polymer had improved toughness measures when evaluated in tension on a Material Testing System (MTS). Despite reducing the crosslink density significantly when formed via this preliminary approach, the thiocarbamate-containing resin had a higher $T_g$ than the PETMP/DVS counterpart. In certain embodiments, when incorporated appropriately without reducing the crosslink density, thiocarbamates increase both $T_g$ and toughness. As illustrated in Table 1, these high toughness, intermediate $T_g$ materials were formed from a flexible tetrathiol and a flexible aliphatic diisocyanate, while only using a difunctional vinyl sulfone. Further, these results suggest that thiol-sulfone/thiocarbamate materials obtained from monomers of higher functionalities and/or monomers having rigid core structures lead to superior toughness polymers as compared to conventional BisGMA systems. In certain embodiments, the PETMP/DVS and PETMP/HMDI/DVS resins are used as model systems in the composite formulation studies as well as in the initial degradability, extraction and lifetime analyses.

An additional composite characteristic is water uptake, which decreases mechanical properties over time. Swelling is an indicator of water sorption, solubility and the potential to extract unreacted monomers from the composite. This issue was investigated by comparing swelling properties of unfilled thiol-vinyl sulfone formulations with the control BisGMA/TEGDMA. Table 2 illustrates the results of water sorption and solubility for unfilled resins. The maximum values of water sorption and solubility for resins are 50 µg/mm³ and 5 µg/mm³, respectively (ISO 9000's standard). In Table 2, both model thiol-vinyl sulfone resins exhibited lower water sorption and water solubility than the control copolymer and the values were well below the range of the ISO 9000s standard. Without wishing to be limited by any theory, swelling properties may be further improved in more crosslinked, higher $T_g$ systems that are more hydrophobic than the present resins.

TABLE 2

Swelling tests show that the thiol-vinyl sulfone and thiocarbamate/vinyl sulfone samples exhibit lower water sorption and solubility than the control BisGMA/TEGDMA.

| Polymer System | Water sorption (µg/mm³) after 70 hr. | Water solubility (µg/mm³) |
|---|---|---|
| BisGMA/TEGDMA | 36.9 ± 1.1 | 2.9 ± 1.2 |
| PETMP/DVS | 23.7 ± 1.9 | 0.5 ± 0.2 |
| PETMP/HMDI/DVS | 27.6 ± 0.8 | 1.8 ± 0.8 |

Example 2

In certain embodiments, the thiol-vinyl sulfone systems of the invention have the ability to react rapidly to high conversion; to achieve, even with flexible monomers, high modulus, $T_g$ and toughness polymers; and to reduce water interactions. These reactions have approximately 60% of the shrinkage per double bond of the corresponding methacrylate polymerization, and proceed via a step growth reaction that leads to lower shrinkage stress due to a delay in the gel point conversion. Without wishing to be limited by any theory, by selecting appropriate multifunctional thiol and vinyl sulfone monomers, enhancements in overall performance metrics and characteristics of dental composites may be achieved relative to the commercial standard methacrylate resins.

Figure 3A:
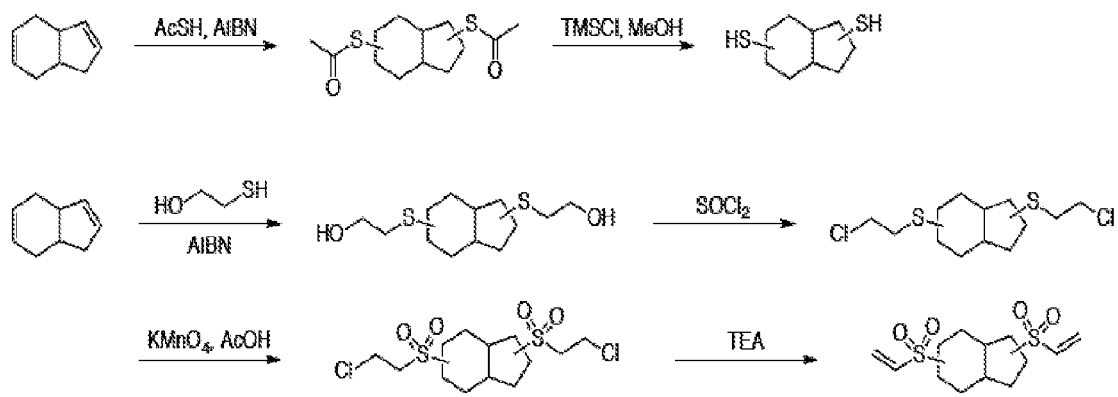
FIGS. 3A-3C illustrate synthetic routes contemplated within the invention. Synthetic route for tricyclodecane based difunctional thiols and vinyl sulfones are described in FIG. 3A.
Figure 3B:
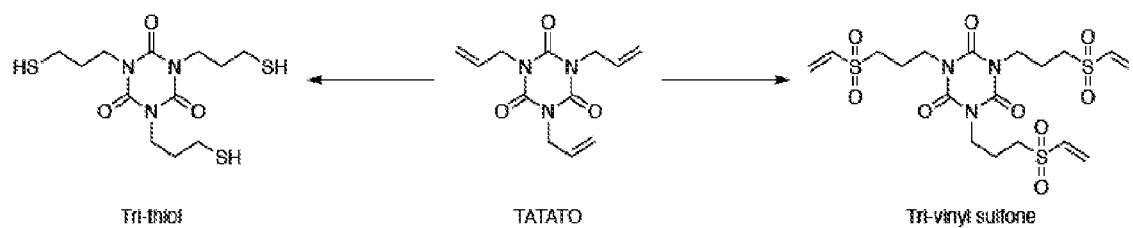
Figure 3C:
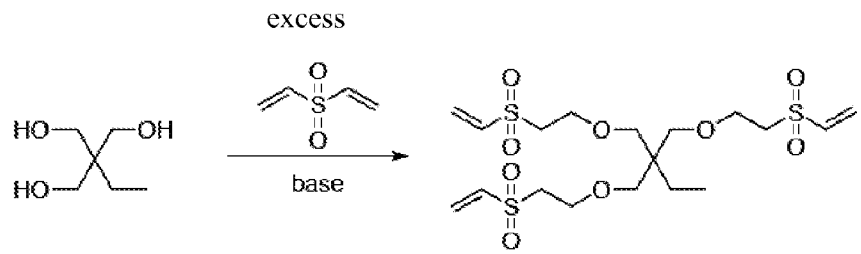

In certain embodiments, to enhance the mechanical and degradation properties of the thiol-vinyl sulfone systems, thiols and vinyl sulfones that do not possess degradable moieties, and may have a rigid backbone, are prepared and used within the invention. FIG. 3 illustrates dithiol and divinyl sulfone monomers without degradable moieties contemplated within the invention. This synthetic methodology may be expanded to design multifunctional thiols and vinyl sulfones. Multifunctional thiols are reacted with diisocyanates (or multiisocyanates to increases crosslink density) to form thiol-functional thiocarbamate-containing monomers. The synthetic methodology illustrated in FIG. 3 may be expanded to any multi-ene to synthesize novel multifunctional thiols and vinyl sulfones. For example, 1,3,5-triallyl-1,3,5-triazine-2,4,6(1H,3H,5H)-trione (TATATO) may be used as a starting material to synthesize rigid core vinyl sulfone and thiol monomers. Alternatively, multifunctional vinyl sulfones are synthesized by incorporating the vinyl sulfone functional group into a molecule that possesses alcohol, thiol or amine groups by a conjugate addition to divinyl sulfone from those functional groups. By implementing this reaction with multifunctional alcohol/thiol/amines, multifunctional vinyl sulfones are obtained. A rigid backbone is incorporated via an aromatic core. For example, a trifunctional vinyl with an aromatic backbone may be used an aromatic multifunctional thiol. This array of approaches to producing multifunctional thiol and vinyl sulfone monomers enables one to circumvent problems that might otherwise arise with the formation of monomer mixtures that would not be soluble, have too high a viscosity, or have other undesirable features such as increasing the swelling behavior. This library of materials is evaluated thoroughly to achieve resin behavior exceeding the BisGMA/TEGDMA control in regards to final conversion, extractables, moisture absorption, shrinkage and stress, flexural strength, modulus, and degradation behavior.

To achieve the desired functional group conversion and mechanical properties in these resin systems, thiol-vinyl sulfone and thiol-vinyl/thiocarbamate resin polymer systems are formulated with catalytic quantities of amines, such as ethyl-p-N,N-dimethylaminobenzoate (DMAB) and nucleophiles such as phosphines. For the reaction kinetics and conversion measurements, FTIR is used to monitor the thiol and vinyl sulfone conversion (middle IR measurements for thin films and near IR for bulk polymerization of thick samples) at various reaction conditions (temperature, catalyst concentration, light intensity for photoinitiated systems, monomer formulation, and so forth). The thiol is monitored at 2,570 cm$^{-1}$ and the vinyl sulfone peak at 1,607 cm$^{-1}$ and/or 3,100 cm$^{-1}$. Without wishing to be limited by any theory, high conversion ensures that the amount of extractables is minimal in these systems, and the extractables from the resin are also quantified. In certain embodiments, stoichiometric mixtures of thiol and vinyl sulfone monomers are formulated with 1 wt % or less (starting at 0.1 wt % and adding a sufficient amount to achieve the maximum conversion) of an amine (DMAB) or a phosphine (methydiphenylphosphine, MDPP) as needed to catalyze complete reaction. Polymerizations are performed, for example, at ambient temperature and 35° C.

Modulus, strength, toughness and $T_g$ are measured utilizing Dynamic Mechanical Analysis (DMA) and a Materials Testing System (MTS). Infrared-based double bond conversion measurements are used for in situ monitoring of polymerization kinetics and to verify the reacted state of samples used for property evaluations. Volume shrinkage is measured using a linometer, while stress measurements are performed on a tensometer. In certain embodiments, shrinkage and stress are lower than the control and shrinkage is below the target 3-8% in resins and 2-4% in composites. Measurement of extractables and degradation products will be made as described elsewhere herein. Swelling and water solubility tests are used to quantify the interactions with water, and the biocompatibility of the system is evaluated through cytotoxicity testing as per ISO 7405 and ISO 10993. The resin performance is evaluated against the control BisGMA/TEGDMA. This methacrylate control is formed via a visible light-initiated chain growth mechanism comprised of a 70/30 BisGMA/TEGDMA resin initiated by a camphorquinone/amine photoinitiator system exposed to light from 400-500 nm. This control is used to benchmark the properties of the thiol-vinyl sulfone systems and to demonstrate their improvements. In certain embodiments, formulations that meet or exceed the performance of the control methacrylate system to the 95% confidence level are considered for further testing. Further, optimal resin systems developed within this aim are used in composite formulations, with improved photoinitiating systems, and/or in the assessment of adhesion and lifetime analysis, including fatigue, wear, and degradation.

Example 3

With the objective of optimizing the integration of inorganic fillers that are compatible with the thiol-vinyl sulfone systems of the invention and do not contain hydrolysable or enzymatically cleavable bonds, several thiol and vinyl sulfone functionalized inorganic fillers are designed and their performances in enhancing the modulus, hardness, toughness, wear resistance, degradation and adhesion at the tooth interface of the composite are evaluated.

Figure 4:
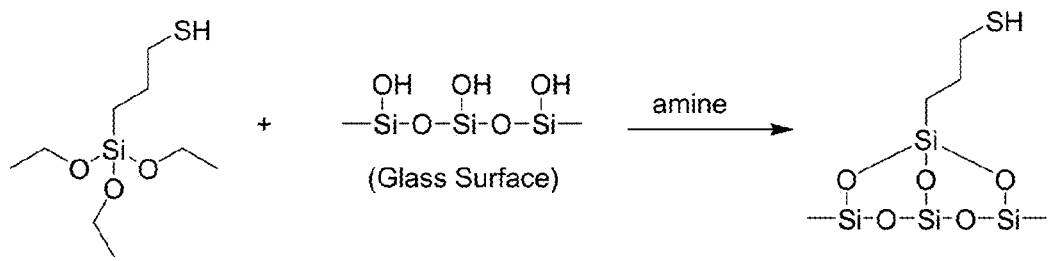
FIG. 4 is a schematic illustration of a mechanism for thiol functionalization on the glass surface via base catalyzed condensation reaction.
Figure 5:
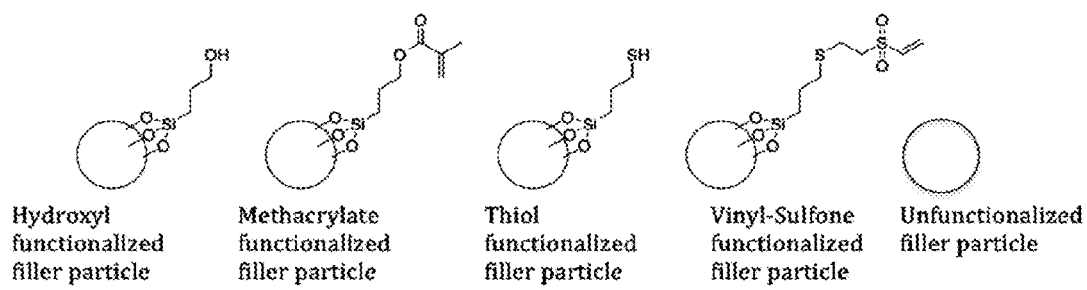
FIG. 5 is a schematic illustration of silica-based filler systems representing particle functionalizations that are formulated and evaluated. In certain embodiments, unfunctionalized and hydroxyl-functionalized particles do not covalently interact with the resin while methacrylates will react to a limited extent and be subject to various degradation mechanisms. In other embodiments, both the thiol- and vinyl sulfone-functionalized particles should copolymerize readily and minimize potential degradation of the interface.
Figure 6:
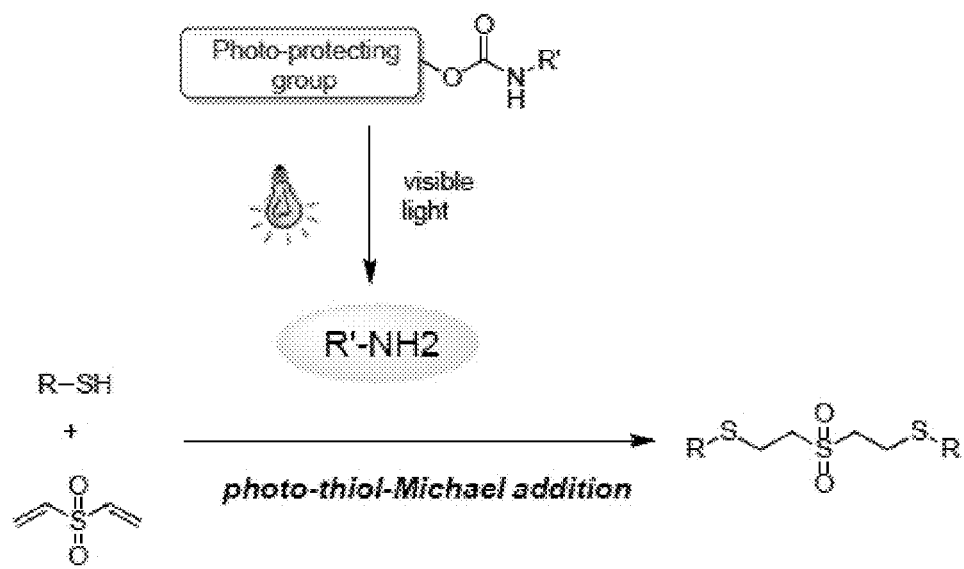
FIG. 6 illustrates a phototriggered thiol-Michael addition reaction using NPPOC-hexylamine as a catalyst.

With the objective of investigating inorganic fillers compatible with thiol-vinyl sulfone systems, several thiol and vinyl sulfone functionalized fillers are designed and their performance evaluated in modulus, hardness, toughness, wear resistance, and adhesion at the tooth interface (FIGS. 4-5). Nucleophiles such as phosphines (triphenyl phosphine, dimethylphenyl phosphine and the like) catalyzed the thiol-vinyl sulfone Michael reaction efficiently. Thus, the reaction between (3-mercaptopropyl) triethoxysilane and excess divinyl sulfone catalyzed by dimethylphenyl phosphine may be used to generate the desired vinyl sulfone silane precursor, which is subsequently reacted onto the particle surface to create the desired vinyl sulfone functionalized fillers.

In one example, thiol and vinyl sulfone functionalized fillers are fabricated by reacting a filler mixture comprised of 90 wt % 0.4 µm glass (Schott) and 10 wt % Aerosil OX50 (nominal size 40 nm) with functionalized silanes. This distribution of filler sizes may ber used as an approximation of practical filler systems. The composite systems are formed via a nucleophilic Michael Addition step-growth reaction with filler loadings varying from 25-80 wt %. Unfunctionalized fillers and fillers functionalized with methacrylates and hydroxyl functional groups are used as controls to ascertain the effectiveness of the thiol and vinyl sulfone modifications. Composite materials are evaluated for fracture toughness (ASTM Standard E399-90, 1997), flexural strength (ISO 4049, ASTM 1997), depth of cure (7.10 of ISO 4049), shrinkage (ISO/DIS 17304) and stress, water sorption and solubility (Water Sorption and Solubility (7.12 of ISO 4049) as well as their fatigue, wear and degradation behavior (as per ISO 14801,ISO/TS 14569-2: 2001). Additionally, the extractables from the composites are also measured, and the biocompatibility of the composite systems are evaluated through cytotoxicity testing (ISO 7405 and ISO 10993).

To pursue the filler development and evaluation simultaneous to the development of new resins, two model thiol-vinyl sulfone resins based on the PETMP/DVS and PETMP/HMDI/DVS resins (Tables 1-2) may be used. These resins may serve for composite evaluation and subsequently as controls for the implementation of new, higher performing resins. To compare composites formulated from resins with dramatically different viscosities, composites are formulated to identical consistency levels rather than identical filler fractions. Consistency is measured by placing a 3.5 kg weight on a 1.0±0.2 cm diameter sample for 3 min and measuring the diameter of the resulting material. Filler loadings are adjusted to maintain consistency across various resin platforms.

Example 4

In certain embodiments, a photoprotecting group that is cleaved when exposed to light to free a highly reactive base catalyst is contemplated. For example, 2-(2-nitrophenyl) propyloxycarbonyl (NPPOC) is an effective protecting group for hexylamine, which is released upon irradiation, and acts as an effective catalyst for the thiol-Michael addition reaction. In certain embodiments, NPPOC-hexylamine can be used as a photo-catalyst in a thiol-Michael photopolymerization reaction in which the tetrathiol PETMP and bisphenol A ethoxy diacrylate (BPAEDA) are reacted to form a crosslinked polymer network with a thiol functional conversion of >80% achieved within the first 10 minutes of the reaction. In other embodiments, N,N-dimethyl pyridine (DMAP) is an efficient catalyst for the thiol-vinylsulfone addition due to the electron donating group at the para position of the pyridine ring. In yet other embodiments, by combining these two motifs (NPPOC protection and DMAP reactivity), a highly efficient, photoprotected catalyst may be identified.

UV-vis spectroscopy is used to measure the absorbance of the compounds, and initiation with 1 wt % of the compounds in PETMP/DVS systems exposed to 10 mW/cm$^2$ of 400-500 nm light is used to evaluate reactivity. Conversion is monitored by FTIR and performance is evaluated as polymerization being complete in under two minutes at these conditions (which are much lower intensity than clinically used). The potential for increasing conversion well into the glassy state and for long times, in contrast to conventional radical polymerizations, is demonstrated by monitoring the conversion in the dark for several hours or days, after a short two minute exposure. Also, depth of cure is monitored to demonstrate dark polymerization. Whereas the polymerization in a radical-mediated reaction (BisGMA/TEGDMA used as a control) is typically minimal and only amounts to a few percent conversion and leads to little enhancement in depth of cure, the presence of any unreacted species in this base-catalyzed system leads to extensive and continuing polymerization after the exposure. This extended polymerization arises because of the persistence of the highly mobile base/nucleophile. As a contingency, if the absorbance band of the photoprotected base does not overlap with the desired wavelengths, two strategies are employed. Chemical modifications that redshift the absorption (e.g., methoxy moieties at the 3- and 4-positions on the nitrobenzene ring) are used, and photosensitizers that absorb the light and transfer the energy, such as camphorquinone or isopropyl thioxanthone, are used.

In addition to the photoprotected bases which may not be sufficiently soluble, reactive or biocompatible, the use of photo-deprotectable nucleophiles comprising either phosphines or nitrogen-centered nucleophiles is investigated, given their ability to initiate the polymerization more rapidly and efficiently. Among phosphines, the triphenyl phosphines, P(4-NMe$_2$Ph)Ph$_2$ are an efficient catalyst with low toxicity and are readily synthesized with O-nitrobenzyl as a photo-removable protecting group. Although the photodeprotection may occur under 320 nm-390 nm exposure and the reaction is slow to achieve over 90% yield, one may (i) shift the absorption wavelengths to the visible and (ii) increase the photoefficiency. As indicated elsewhere herein, the absorption maxima are shifted by chemical modifications to the NPPOC or the use of visible light sensitizers. The quantum yield and efficiency of the photodeprotection is enhanced by improving the quality of the leaving group through methyl substitutions of the NPPOC.

Alternatively, strategies for protecting (and the ultimate photoinduced deprotection) of nitrogen-centered nucleophiles may be explored. UV-vis spectroscopy is used to measure the absorbance of these compounds and initiation with 1 wt % of these compounds in PETMP/DVS systems exposed to 10 mW/cm$^2$ of 400-500 nm light is used to evaluate reactivity. Conversion is monitored by FTIR and performance is evaluated as polymerization being complete in under two minutes at these conditions.

Example 5

The 2-nitrobenzyl functional group is a photolabile protecting group utilized in organic synthesis, being utilized as protective group for functional groups such as OH, NH$_2$, SH, and COOH. Further, 2-nitrobenzyl derivatives with better quantitative yields and photolytic efficiency, such as 2-nitroveratryloxycarbonyl (NVOC) and 2-(2-nitrophenyl) propyloxycarbonyl (NPPOC), have been used as primary amine protecting groups for spatioselective surface functionalization and photolithographic synthesis of oligonucleopeptide/peptide microarray. NPPOC has a higher quantum yield during photolysis than NVOC.

As discussed elsewhere herein, primary amines, such as hexylamine, are efficient catalysts for the thiol-Michael addition in macromolecular synthesis, but lack the spatiotemporal control afforded by photoinitiation. In one aspect, NPPOC is an effective protecting group for hexylamine, which is released upon UV irradiation to catalyze the thiol-Michael addition of a thiol and acrylate.

Synthesis:

2-(2-Nitrophenyl)propyl chloroformate in $CH_2Cl_2$ was added dropwise to a stirred solution of hexylamine (2 mmol) and DIPEA in $CH_2Cl_2$ at 0° C. The reaction was stirred at room temperature for 8 hours. The mixture was washed with brine and dried with anhydrous $Na_2SO_4$. The crude product was purified by silica gel column chromatography using hexane: EtOAc (1:1) to afford a pure product (76%) as light yellow oil (FIG. 7A).

Photolysis:

NPPOC-Hexylamine was dissolved in MeOH (10 ml) and then stirred under 320-390 nm irradiation (20 mW/cm$^2$) for 3 hours (FIG. 7B). After irradiation, a 100 μl aliquot was diluted to 10 ml (0.05 mM) in MeOH and upon which a UV/Vis spectrum was obtained (scanning 1 nm/s from 200 to 600 nm) (FIG. 7C).

Tests:

To demonstrate the potential of NPPOC-hexylamine as a photocatalyst for the thiol-Michael addition reaction, thiol glycolate and methyl acrylate were selected as model substrates (Table 3). The model reaction showed over 90% yield in 1 h, indicating this catalytic reaction proceeded rapidly and efficiently. Control experiments (entry 6 and 7) indicated that both the photolabile catalyst and photo-irradiation were important to trigger this reaction.

Figure 7D:
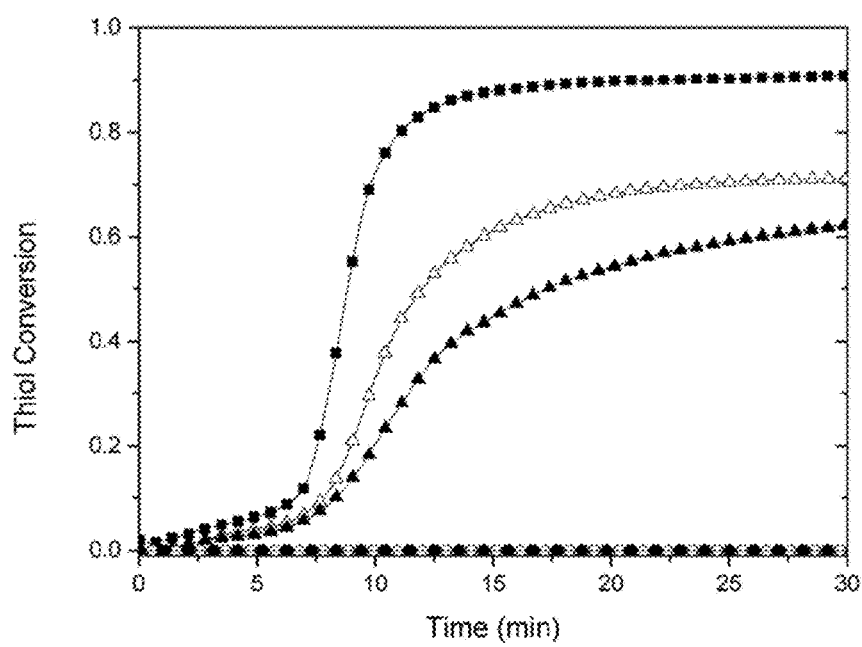

Kinetics Tests:

Reaction kinetics were monitored by FT-IR spectroscopy at a series scan rate of one scan per 2 seconds (FIG. 7D). These studies were performed on a Nicolet 750 *Magna* FT-IR spectrometer with a KBr beam splitter and an MCT/A detector under dry air. Samples were sandwiched between to NaCl windows and placed into a horizontal transmission apparatus. The sample thicknesses were approximately 200 microns. The conversion of thiol and vinyl functional groups was assessed by monitoring the disappearance of peak areas centered around 2567 and 812 cm$^{-1}$, respectively.

Figure 7E:
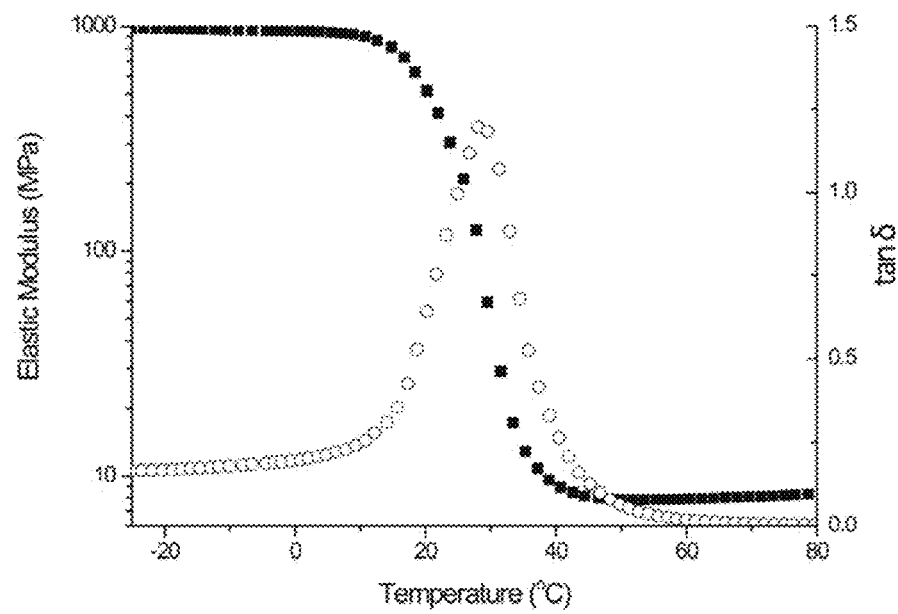
Figure 7F:
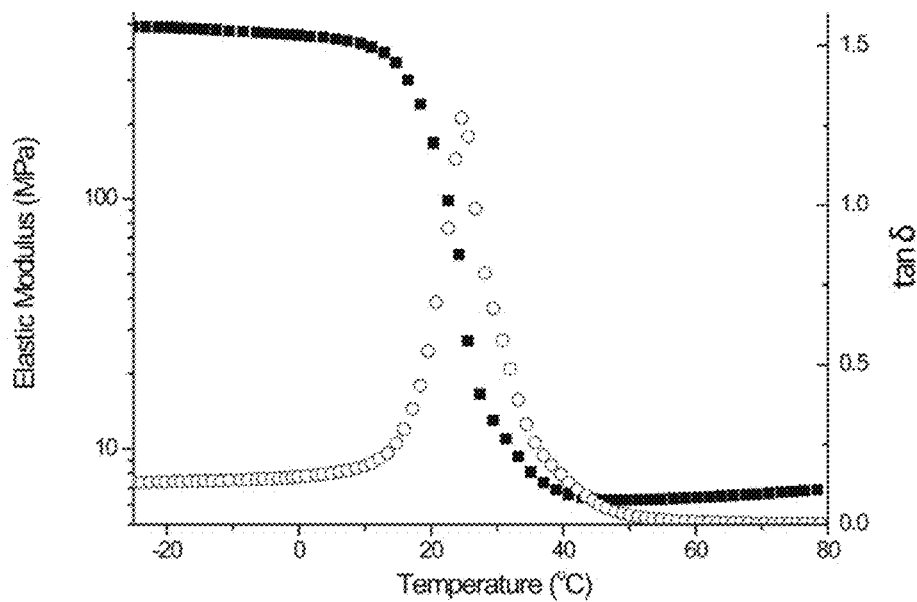
Figure 7G:
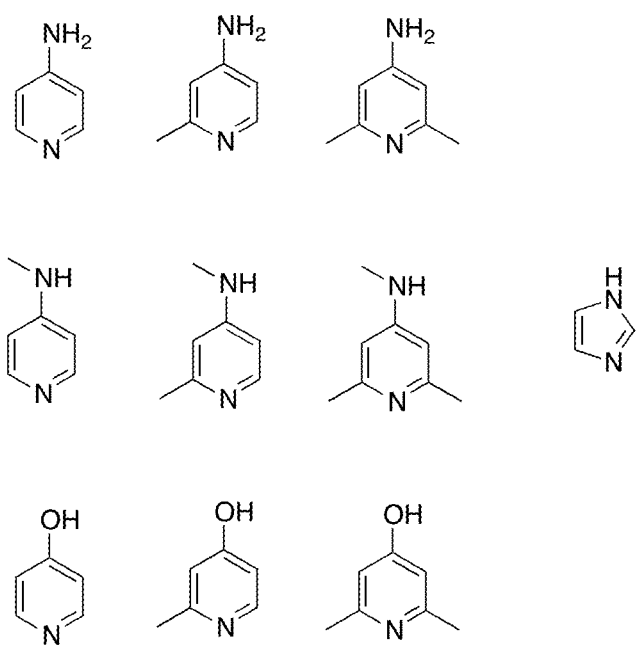
Figure 11:
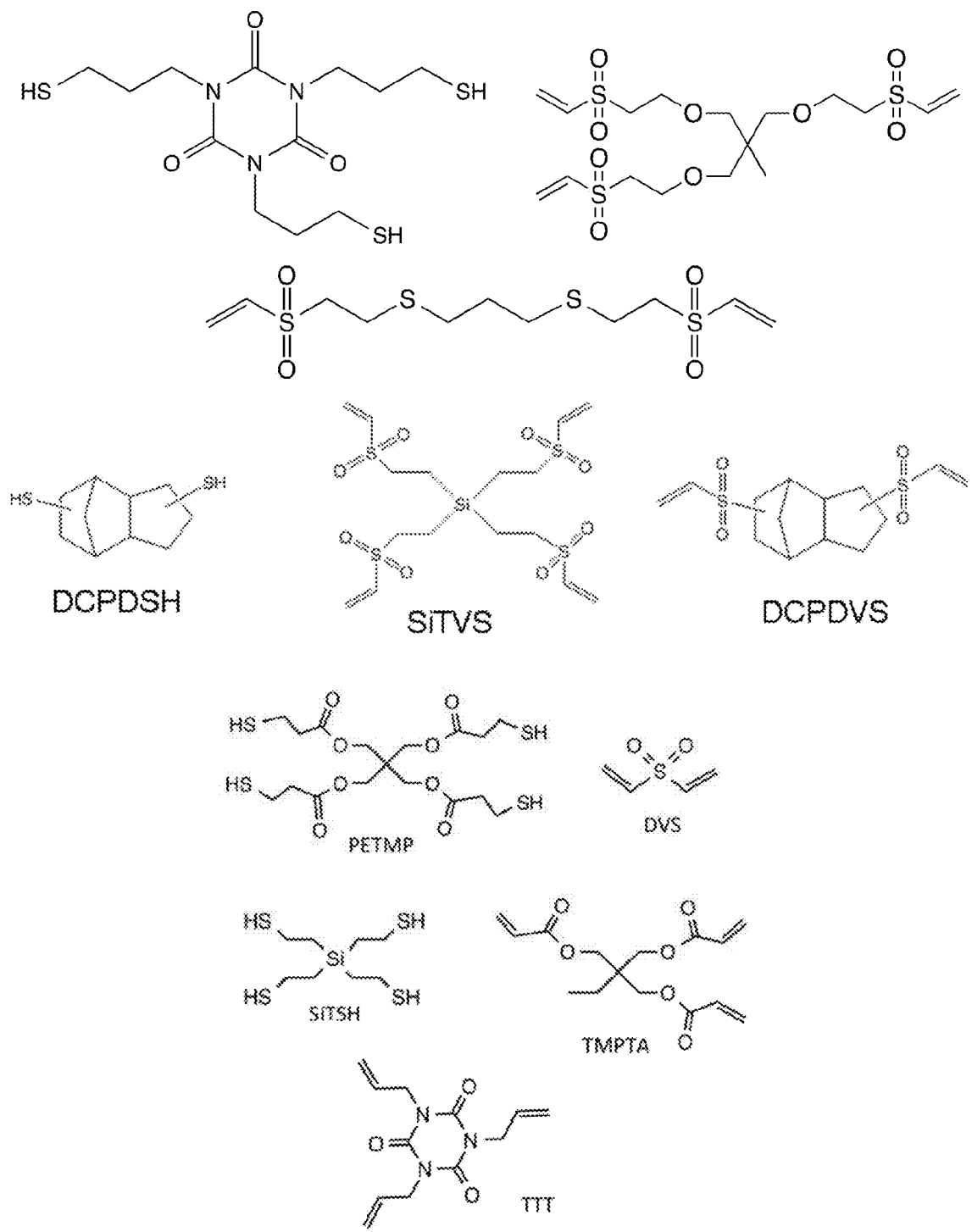
FIG. 11 illustrates monomers useful within the invention.
Figure 12:
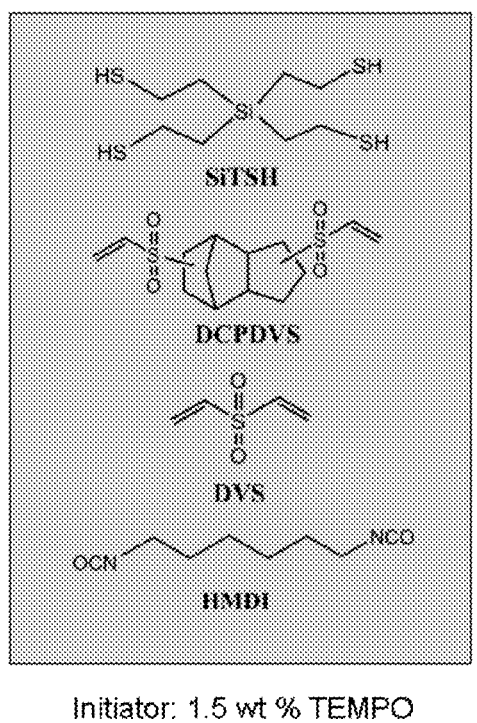
FIG. 12 illustrates characterization of compositions of the invention.

Networks Formation:

NPPOC-hexylamine acted as a photo-catalyst for the thiol-Michael photopolymerization reaction. Two tetrathiols (PETMA and PETMP) and a bisphenol A ethoxy diacrylate (BPAEDA) were selected as substrates for the polymer network formation. To mitigate the side effects of $CO_2$, which was released during photolysis, the NPPOC-hexylamine concentration was decreased from 5 to 3 mol % and the irradiation time was extended to 1 hour. While similar, the resulting polymer networks exhibited a slight shift in glass transition temperatures as determined using dynamic mechanical analysis (DMA) via the peak in the tan δ curve (i.e., 29 and 25° C. for the PETMA/BPAEDA, FIG. 7E, and PETMP/BPAEDA, FIG. 7F, respectively). The larger elastic moduli in the rubbery region for the PETMA-versus PETMP-based material suggests an increased crosslink density (0.95M versus 0.77M at 80° C.), which is attributed to the shorter distance between crosslinks in the PETMA system. In either case, the narrow tan δ peaks indicated a homogeneous polymer network as observed in other thiol-ene photopolymerization reactions.

TABLE 3[a]

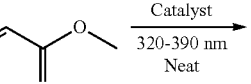

Catalyst:

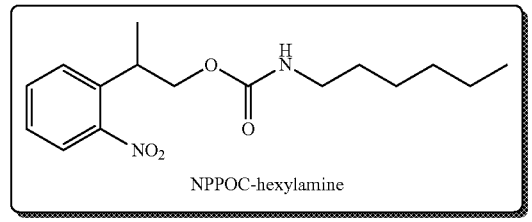

| Entry | R—SH | Catalyst Loading (mol %) | Irradiation Time (min) | Yield[b] (%) |
|---|---|---|---|---|
| 1 | 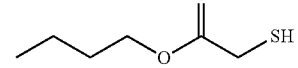 | 5 | 60 | 93 |
| 2 | 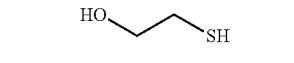 | 5 | 60 | 94 |
| 3 | 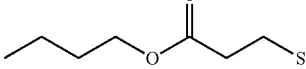 | 5 | 60 | 91 |
| 4 | 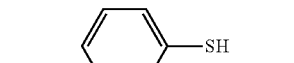 | 5 | 90 | 93 |
| 5 |  | 1 | 90 | 55 |
| 6 | 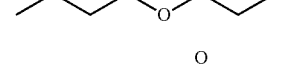 | 5 | 0[c] | 0 |
| 7 | 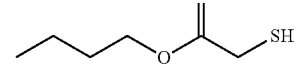 | 0 | 90 | Trace |

Example 6

The combination of a photogenerated nucleophile/base-initiated Michael addition reaction with a photoinitiated radical-mediated thiol-vinyl reaction could achieve high conversions in a relatively short time in addition to ensuring that the reaction conditions remain within clinically acceptable parameters. A dual approach to in-situ curing may ensure a rapid reaction rate, minimal initiator and nucleophile concentrations, enhanced cure depth and dark cure with superior adhesion between the composite and tooth enabled by the radical-mediated reaction mechanism. Thus, the combination of catalysts for these two reactions may improve the reaction kinetics, and yield higher conversions and overall improvements in behavior.

TABLE 4

A comparison of the reaction kinetics between the visible-light initiated polymerization of a thiol-vinyl sulfone model system using TPO and a phosphine catalyzed thiol-vinyl sulfone indicate that high functional group conversions were obtained by both systems.

| PETMP/DVS (thiol-vinyl sulfone) | Visible light initiated polymerization | Nucleophile (Methyldiphenylphosphine) initiated polymerization |
|---|---|---|
| Thiol conversion | 74% | 80% |
| Catalyst concentration | 2 wt % | 0.1 wt % |
| Reaction time | 2 min. | 1 min. |

Table 4 exemplifies that the thiol-vinyl sulfone reaction can be photoinitiated. These thiol-vinyl sulfone polymerizations were initiated via a conventional radical-based photoinitiator (TPO, ethyl 2,4,6-trimethylbenzoylphenylphosphinate) and yielded model crosslinked networks with high conversion. The MDPP-catalyzed reaction (not photoinitiated) is illustrated for comparison, demonstrating that base-catalyzed reactions may achieve higher conversions in these glassy polymers. In certain embodiments, rapid reaction may be achieved based on the efficiency of the radical photoinitiation scheme and high conversion based on the persistence and high mobility of the base-catalyst. Formulations for such study include the model PETMP/DVS and PETMP/HMDI/DVS monomer resins and composites, and allow for evaluating the efficacy of 1 wt % TPO as a radical initiator in achieving an appropriate rate, depth of cure (ISO 4049 7.10), and final conversion. The photobases useful within the invention may be combined at appropriate levels with the radical photoinitiators. If the rate is insufficient in the presence of TPO, the more efficient germanium-based initiators may be used to increase the rate of the radical-mediated thiol-vinyl reaction. In certain embodiments, the results are monitored in search of a 2× reduction in extractables and formation of a glassy polymer in the same time that the control, BisGMA/TEGDMA resins and composites achieve complete reaction. The depth of cure may also be greater in these thiol-vinyl sulfones.

Adhesion.

In certain embodiments, the photobase/nucleophile achieves sufficient extent of reaction and cure speed all by itself. In other embodiments, the use of the radical photoinitiator may be considered. The thiolate anion that serves as the reactive intermediate in either the base- or nucleophile-catalyzed reaction is unlikely to react to a significant extent with the methacrylates present in common commercial adhesive formulations. To assure proper integration of these thiol-vinyl sulfone composites, they must be compatible with the currently used adhesive formulations, even though those cure through a different mechanism (i.e., the radical polymerization of the methacrylates). The presence of radicals in the polymerization, along with the base/nucleophile, enables thiol-methacrylate radical reactions to occur, leading to the formation of a strong covalent bond between the composite and the adhesive. The role of the radical and nucleophile is each evaluated by eliminating one and then the other. Further, the importance of long term reaction is evaluated by studying the temporal evolution of adhesion as a function of time both in the presence and in the absence of the nucleophile. If the initial or long term adhesive force is less than that of the methacrylate control, monomers that contain both vinyl sulfone and methacrylate functional groups are incorporated as agents that can copolymerize both via the thiol-vinyl sulfone reaction in the composite and the methacrylate polymerization in the adhesive. These agents would serve to enhance the number and nature of the covalent bonds that span from the composite to the adhesive.

The successful adhesion of the thiol-vinyl sulfone to the tooth structure is evaluated by using a commercially available adhesive bonding system and compared to adhesion using the control BisGMA/TEGDMA composite. The initial formulations consist of PETMP/DVS and PETMP/HMDI/DVS as presented with 1 wt % TPO used as the photoinitiator along with the presence of 0.1 wt % MDPP as a nucleophile catalyst with exposure to 10 mW/cm$^2$ light from 400-500 nm for varying lengths of time. Thiol-modified filler is used to formulate the initial composites. Improvements in monomers, initiators and filler technologies are incorporated and evaluated as soon as developed. All results are compared to the BisGMA/TEGDMA control composite as well as these initial model composites.

Specifically, adhesion is evaluated through Watanabe's "single plane shear test." Teeth are kept in water until the bonding process begins after which they are mounted. A Mylar sheet with an appropriate sized hole (e.g., 50 µm) is placed on top and used to assure that the adhesive area is limited, consistent and known. Then, a second Delrin block with a larger hole is screwed into place. The exposed area is then etched followed by application of the commercial adhesive according to the manufacturer's protocol followed by curing of the composite in the larger hole. Initial adhesion testing will involve storing the samples in water at 37° C. for 24 hours before measuring the adhesive force. For those samples that demonstrate adhesion at least as strong as the controls, extended aging and evaluation in multiple challenge conditions are undertaken. Specifically, the samples are incubated at 37° C. for 90 days in pH 4 buffer, artificial saliva and esterase solutions prior to evaluating the adhesion behavior. At each end point, the blocks are removed from the sample and the force required to fail the adhesive bond is measured. The adhesive bond strength is the force required to break the samples apart divided by the adhesive area associated with the smaller hole. A minimum of 10 samples is tested for each formulation as is needed for appropriate discrimination.

Example 7

The formulation of thiol-vinyl sulfone resins into a photocurable composite is a novel approach to the development of new dental restoratives. These materials are evaluated to demonstrate that they result in dental composites that exhibit at least a two-fold increase in lifetime, as demonstrated by wear and fatigue characterization, and to demonstrate that the thiol-vinyl sulfone chemistry results in increased long-term biocompatibility, as indicated by reduced degradation and extraction products. Over time, dental restoratives are susceptible to hygroscopic release of unreacted extractables as well as hydrolytic degradation products. The mechanism and amount of release varies depending on the chemistry, structure, and overall conversion. Additionally, composite degradation occurs via dissolution, hydrolysis, and wear and erosion from chewing or grinding. The effects of extractable and degradation products on the body and long term performance include reduced composite service lifetimes associated with secondary caries mediated by accelerated bacterial linked to various components of the composite and immune responses have also been observed. In vitro testing is used as an imperfect, but most practical, mimic for in vivo performance, where it is used as a practical screening and ranking tool for composite evaluation.

The ester linkages that are necessarily present in methacrylate resins are susceptible to hydrolytic degradation. The novel thiol-vinyl sulfone systems of the invention do not contain ester linkages and will lead to an overall composite system without hydrolyzable groups, leading to dramatically reduced levels of hydrolytic and enzymatic degradation of both the crosslinked polymer and at the filler resin interface. Hydrolysis is simulated in vitro through appropriate aqueous, salivary, enzymatic, and pH environments. Further, the step growth nature of the polymerization and the covalent integration of inorganic fillers results in a composite system with high functional group conversion and concomitant low levels of extractables as well as excellent mechanical properties. Without wishing to be limited by any theory, these properties allow for reduced extractable and degradation products, wear, and susceptibility to fatigue, thereby enabling increased service lifetimes by at least two-fold.

Utilizing the PETMP/DVS and PETMP/HMDI/DVS model systems, baseline testing is performed on resin and composite systems to evaluate cytotoxicity, degradation, wear, and fatigue. The initial baseline evaluations utilize the filler composition with the thiol-modified surface. These evaluations serve to compare to the BisGMA/TEGDMA control system as well as to help guide further monomer developments. Successful formulations are further evaluated utilizing the initiation systems developed elsewhere herein.

Lifetime Analysis.

Extractable and degradation products are examined utilizing artificial saliva, esterase, and pH 4 solutions. This approach of using three challenge solvents is expected to fully probe the type and levels of extractable and degradation products and to develop direct comparisons to the BisGMA/TEGDMA controls. In addition to testing degradation products from bulk samples, specimens with increased surface area, to accelerate degradation, are formed by grinding the samples. HPLC is utilized to measure and analyze the products. The non-ester containing thiol-vinyl sulfone systems are expected to exhibit dramatically reduced levels of hydrolytic degradation products. Analysis of the soluble products are conducted on all formulations that achieve improved conversion and equivalent mechanical properties to the BisGMA/TEGDMA controls to enable the identification of degradation products that guide further optimization and changes of the thiol and vinyl sulfone monomers. Initially, resin and composite formulations are cured utilizing dental amines and nucleophiles. Subsequently, formulations are cured utilizing photoprotected base/nucleophiles and photogenerated base/nucleophile and radical initiator combinations. Degradation testing is conducted on all formulations that demonstrate at least a two-fold decrease in extractables relative to controls. In certain embodiments, formulations demonstrate at least a 2-fold improvement over the control by exhibiting less than 50% of the degradation levels of the BisGMA/TEGDMA system after 90 days in each of the challenge solutions, both in thin films and in high surface area powders.

Wear and fatigue testing is performed on model systems compared to the BisGMA/TEGDMA controls to evaluate correlations between fatigue, wear, and mechanical properties. Formulations and initiator systems are characterized for polymerization kinetics, final conversion, mechanics, shrinkage and stress, moisture uptake, and extractables. Formulations that achieve at least equivalent mechanical properties to the controls are characterized for wear and degradation. Successful formulations that achieve wear and degradation properties exhibiting at least a 2-fold improvement over the BisGMA/TEGDMA controls are characterized for fatigue. In certain embodiments, formulations demonstrate at least a 2-fold improvement in wear resistance, a 2-fold decrease in extraction and degradation products, and achieve at least twice the number of cycles before failure at an equivalent load over the control. This combined behavior may yield at least a twofold increase in service life.

Testing Protocols:

Fatigue (Long Term Performance):

A critical component of the determination that a composite material achieves an increase in service life is the application of a cyclic stress/strain to that restoration. The application of a cyclic strain and the subsequent material evaluation is used as a means for simulating and predicting the service life of dental composites. The cyclic strain is used to evaluate the effect of cumulative damage on the samples in a mimic of the chewing and grinding activity to which a restorative is cyclically exposed in vivo. Composite samples are tested in deionized water using staircase sensitivity statistical design. Materials are cycled 500,000 times each and the load is stepped up (or down) based on the success or failure of the previous sample. For a particular composition, 20 samples (ISO 4049) are required to determine the mean and standard deviations of the failure load. The samples are tested with step sizes of either 20N or 50N and at strain rates of 20 Hz, though an analysis of the appropriateness of these conditions is performed to, for example, determine whether there is strain rate sensitivity. The number of cycles to failure is analyzed with the means compared via ANOVA/Tukey with a 95% multiple range test. Clinically relevant loading limits (~30-60 MPa) are used. Selected samples are evaluated after 90 days of aging in the various discussed challenge solutions prior to evaluation for fatigue.

Wear (Long Term Performance):

A 3-body wear machine (Oregon Health Sciences University Oral Wear Simulator) is utilized in evaluating wear on dental composites. Specimens are subjected to three-body abrasion with an abrasion load of 20 N and an attrition load of 70 N at a frequency of 1.2 Hz and 50,000 cycles. Successful formulations exhibit less than half of the wear of the control BisGMA/TEGDMA system.

Extractables and Degradation:

Monomer and polymer stability towards extractables and degradation is tested by subjecting individual monomers and polymerized samples for 7 and 90 day exposures at 37° C. to three challenge solvents: artificial saliva (aqueous solution prepared with 0.4 g/l NaCl, 0.4 g/l KCl, 0.795 g/l CaCl $PO_4.2\ H_2O$, 0.78 g/l $NaH_2PO_4.2H_2O$, 0.005 g/l $Na_2S.9H_2O$, and 1.0 g/l $CO(NH_2)_2$), enzymatic esterase solutions, and pH 4 phosphate buffer solution. Mass loss is measured according to ISO 4049-7 to determine the amount of extractables. Results for both polymer and composite samples are compared to resin composite controls. In addition to testing thin films, to maximize extraction and degradation rates, a comparison of the degradation performance of those films with solid samples that are ground with a ball mill is performed. The degradation and extraction products are evaluated by HPLC and/or extracted into ethyl acetate, dried, and then mixed with methanol for analysis by LCMS to detect degradation and extraction products. In certain embodiments, formulations exhibit less than half of the extractables and degradation products of the control BisGMA/TEGDMA.

Cytotoxicity/Biocompatibility:

Both polymer and composite samples are tested for cytotoxicity using the ISO 10993: Biological evaluation of medical devices, Part 5: Elution Method (L-929, mouse fibroblast cells; 1×MEM extract—24 hour exposure). Samples are sent to NAMSA for cytotoxicity testing. Results for both polymer and composite samples re compared to control BisGMA/TEGDMA polymer and composite controls. In certain embodiments, formulations exhibit a grade 0 cytotoxicity.

Example 8

Pentaerythritoltetra(3-mercaptopropionate) (PETMP) is a thiol ester derivative commonly used in crosslinking thiol-ene or thiol-Michael reactions. Most other commercially available thiol monomers are either thioacetates or other thiopropionates. Their use does not allow for a control in the ester loading through variations in monomer structure or monomer selection. As demonstrated herein, six thiol-ene/thiol-Michael mixtures with varied ester content were prepared to assess the resins curing behavior and the resulting materials' mechanical properties and hydrolytic stability. For the latter, solvent resistance tests in 10% acidic (HCl) and 10% basic (NaOH) solutions over the period of three months were performed.

To enable a better adjustment of the ester content, an ester-free tetrathiol was synthesized using tetravinyl silane and thioacetic acid as the starting materials. The synthesized tetra(2-mercaptoethyl)silane is an alkyl thiol of relatively low molecular weight (272.2 g/mol), which is almost half of the PETMP molecular weight. It was found to have one order of magnitude lower viscosity than PETMP (Table 5), which in certain embodiments facilitates composite mixture handling and processing of mixtures before and during polymerization. As illustrated in Table 5, all formulations containing SiTSH exhibit significantly lower viscosities in pair-wise comparisons with PETMP.

TABLE 5

The ambient temperature viscosities of the tested thiols as well as thiol compositions. Standard deviations are included in the brackets.

| Monomer/Formulation | Viscosity (mPa · s) |
|---|---|
| SiTSH | 65 (1) |
| PETMP | 369 (1) |
| SiTSH + DVS | 8.7 (0.3) |
| PETMP + DVS | 30.2 (0.5) |
| SiTSH + TMPTA | 65 (2) |
| PETMP + TMPTA | 184 (1) |
| SiTSH + TTT | 96 (3) |
| PETMP + TTT | 332 (3) |

PETMP and SITSH were both stoichiometrically reacted in thiol-Michael reactions with TMPTA and DVS, as well as in radical thiol-ene reactions with TTT. Therefore, from six different monomer systems, two (SITHS/DVS and SITSH/TTT) contained no interchain ester linkages at all. On the other hand, the highest ester content occurs for the PETMP/TMPTA system. Regardless of the reaction type, the polymeric samples were cured in pairs (and/or postcured) in the same way to enable unbiased data comparison. To prepare the thiol-Michael polymers, TEMPO (1 wt %) was used as base/nucleophile initiator and the reactions were carried out at 90° C. The kinetic analysis confirmed a stoichiometric reaction (FIG. 14C) between thiols and double bonds. TEMPO can abstract hydrogen from protic species, and the thermal decay of TEMPO may involve hydroxylamine generation, which in this case may serve as a base to accelerate the thiol-Michael reaction. The radical thiol-ene systems were cured with the visible light initiator BPO (1 wt %) at ambient conditions.

Figure 14A:
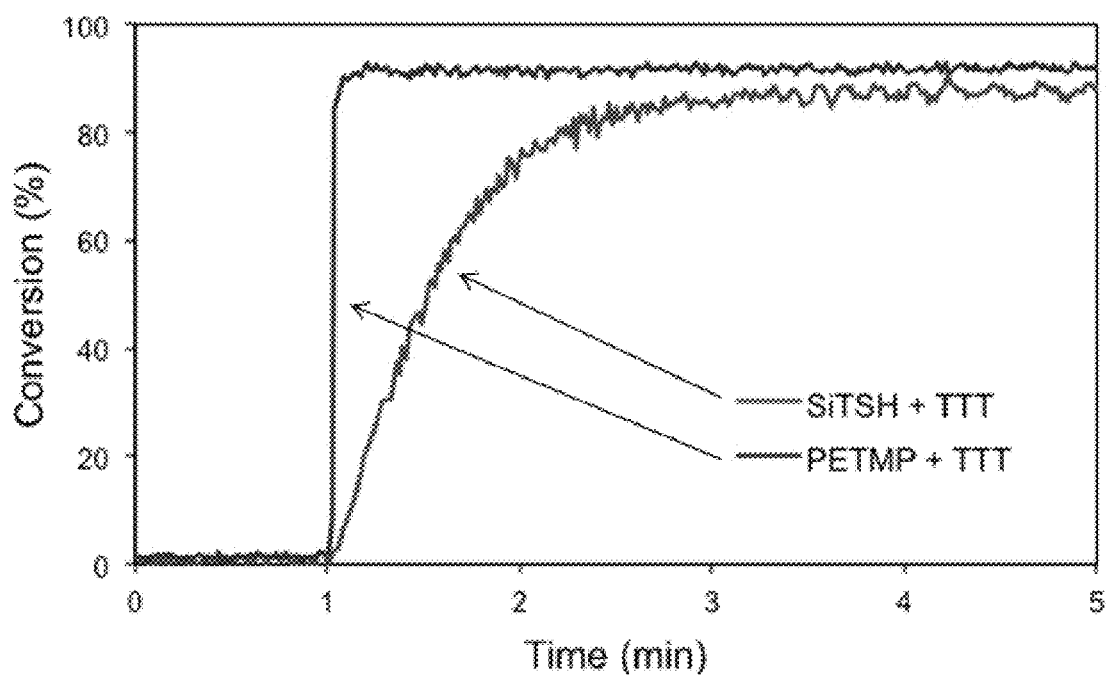
Figure 14B:
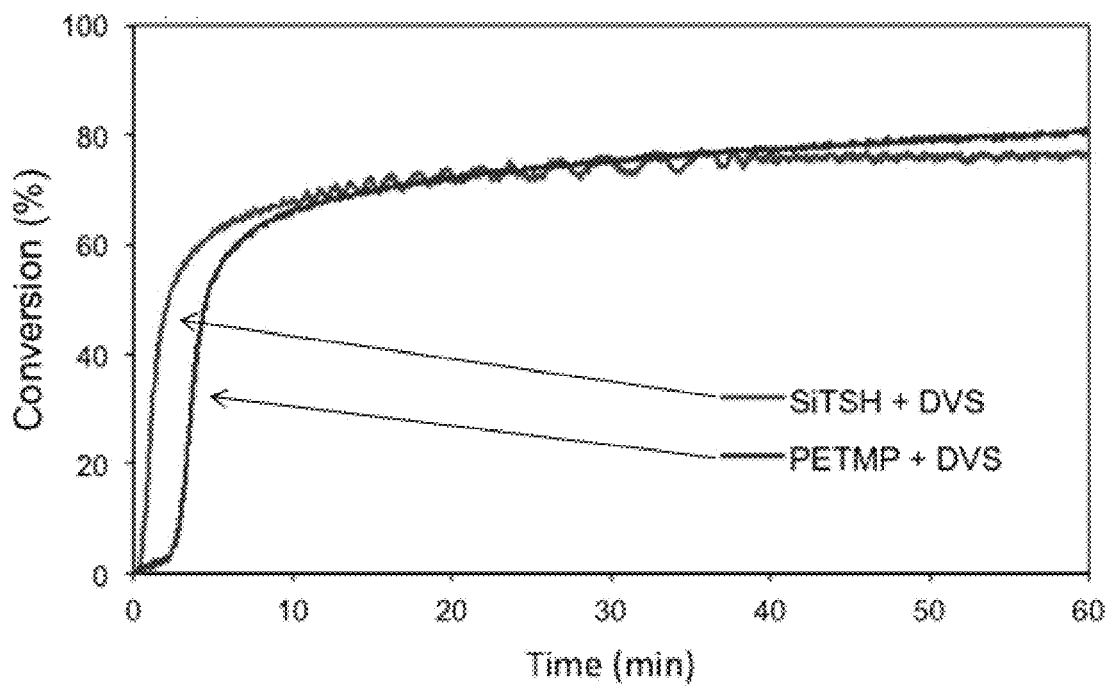
Figure 14C:
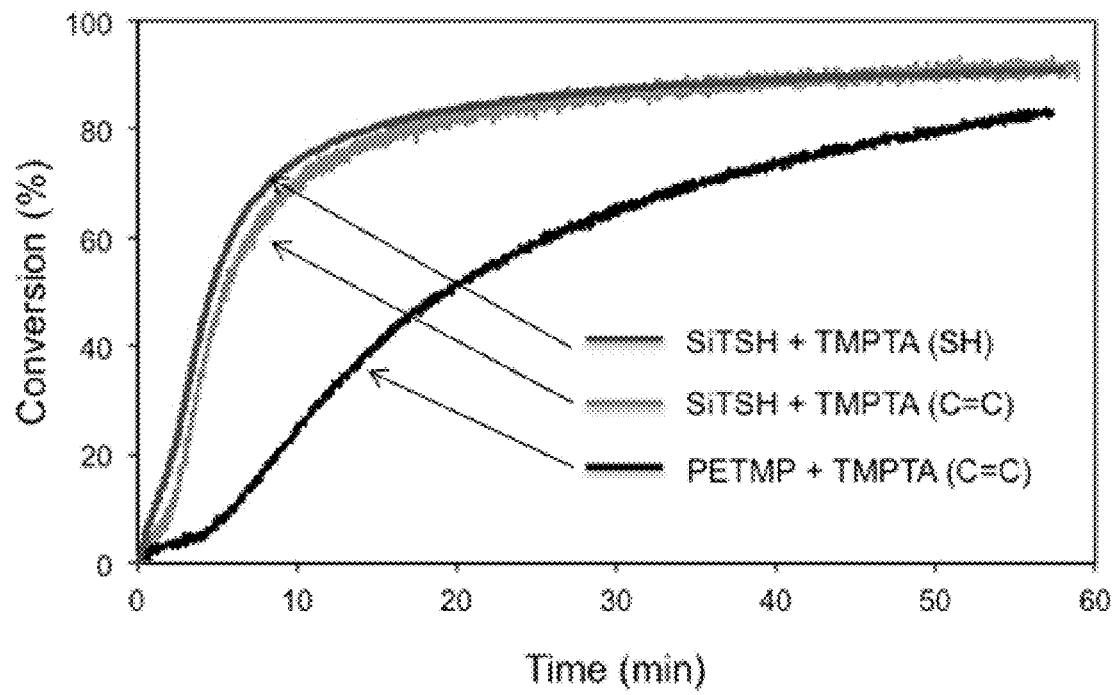

The relevant kinetic plots for thermally and photochemically initiated polymerizations are depicted in FIGS. 14A-14C. Maximal reaction rates obtained between 10-40% double bond conversions are summarized in Table 7. Comparing the thiol and double bond consumption rate for SiTSH/TMPTA system in FIG. 14C, it was observed that the monomers reacted stoichiometrically when TEMPO was used and the reaction was initiated thermally. The maximal double bond consumption rate was one order of magnitude faster for the silane thiol/acrylate mixture indicating higher reactivity of SiTSH when compared to PETMP (Table 7). The thiol-Michael reactions were even more rapid when DVS is used as Michael acceptor (FIG. 14B, Table 7). Without wishing to be limited by any theory, the rate of the silane thiol-divinyl sulfone reaction may be too rapid to yield a crosslinked polymer when initiated with weak nucleophiles/bases such as triphenylphosphine and triethylamine. In certain embodiments, TEMPO acted as a very weak base, and the elevated temperature accelerated the polymerization enabling high functional group conversions. Consistent with this observation, a slow reaction resulting in ultimate gelation was observed when the SiTSH/DVS TEMPO-containing mixture was shelf-stored at ambient temperature for a couple of hours.

Fairly high conversions were achieved in the tested thiol-Michael formulations, which usually exceeded 80% after one hour in the heating compartment in the IR instrument. On the other hand the silane thiol (an alkyl thiol) reacted with lower reaction rates in radical thiol-ene polymerization (0.072 mmol·s$^{-1}$ as opposed to 0.386 mmol·s$^{-1}$ for PETMP/TTT) but could be reacted to high conversions over relatively short time. Further, after thermal annealing of the samples at 100° C. for an additional hour, near-quantitative conversions were achieved (Table 6).

Figure 15A:
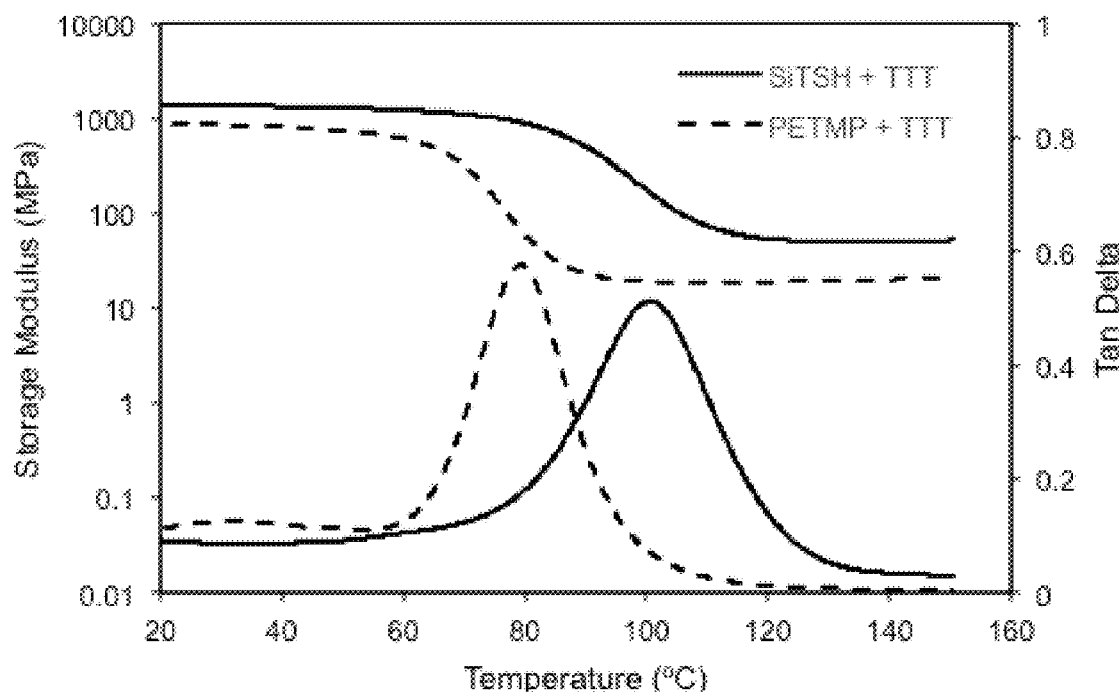
FIGS. 15A-15C illustrate storage modulus and loss tangent (tan delta) plots for (FIG. 15A) SiTSH/TTT and PETMP/TTT radical thiol-ene networks.
Figure 15B:
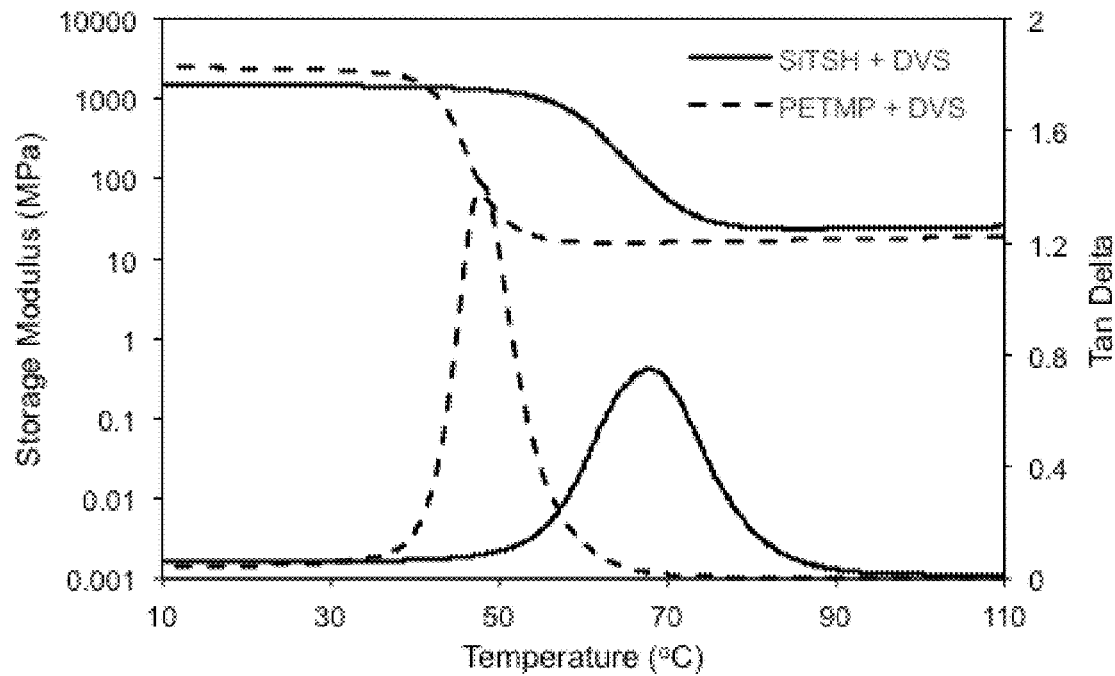
Figure 15C:
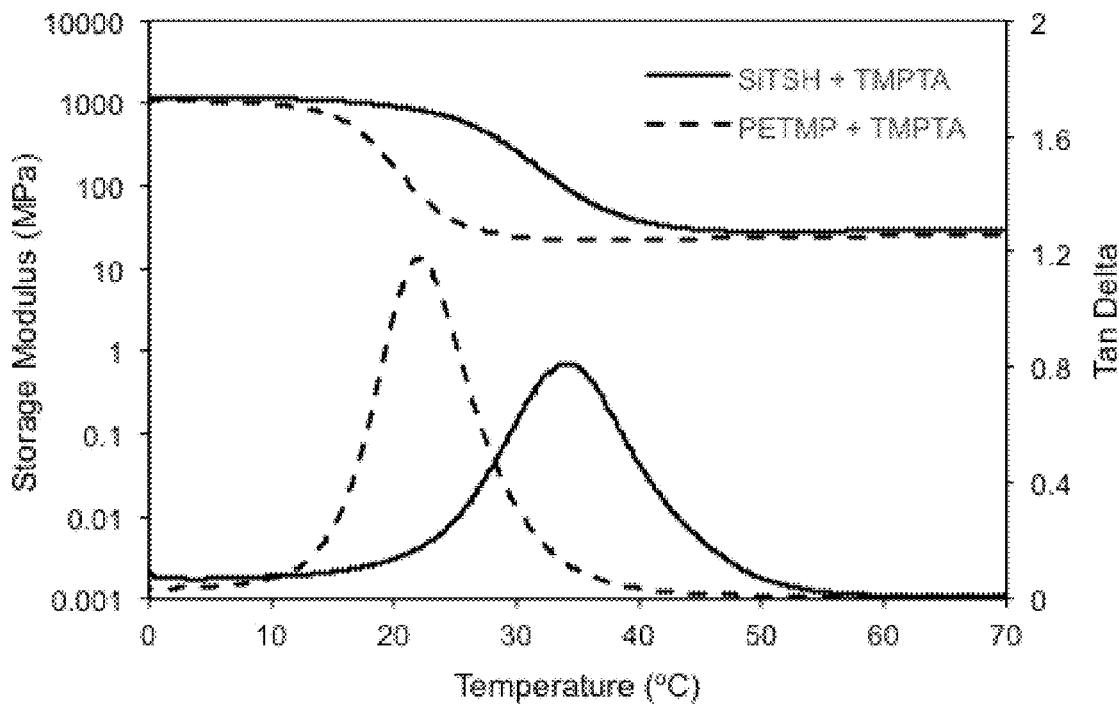

Viscoelastic properties were analyzed by DMA on thermally postcured samples (FIGS. 15A-15C). All formulations created fairly homogenous networks, as indicated by the narrow tan delta peak widths. ($T_{g1/2width}$~20-30° C.), consistent with step-growth systems. Interestingly, the networks containing SiTSH achieved significantly higher glass transition temperatures and rubbery moduli (i.e., crosslinking density) compared to using PETMP. Without wishing to be limited by any theory, this result may relate to better crosslinking capability of the low molecular weight silane tetrathiol as well as the reductions in ester content in SiTSH-containing formulations. Also, in this case the DVS-derived networks exhibit higher $T_g$'s than the networks based on TMPTA. However, the highest glass transition temperatures were achieved for the two thiol-ene systems, most probably due to the highly crosslinked structure of these, and the rigid segments provided by the TTT monomer. It is worth noting that depending on the conversions, $T_g$'s exceeding 100° C. are obtained for SiTSH/TTT composition and this performance was achieved without the use of excessively viscous resin mixtures. Therefore, the silane thiol presented herein is a promising crosslinking candidate for coating, lithography and dental resin applications as it allows for the generation of glassy thiol-ene systems even when the curing is performed at ambient conditions. In certain embodiments, its additional advantage, besides the absence of relatively "soft" and hydrophilic ester groups, is very low viscosity, which helps increase the filler loading in any composite material.

Figure 17:
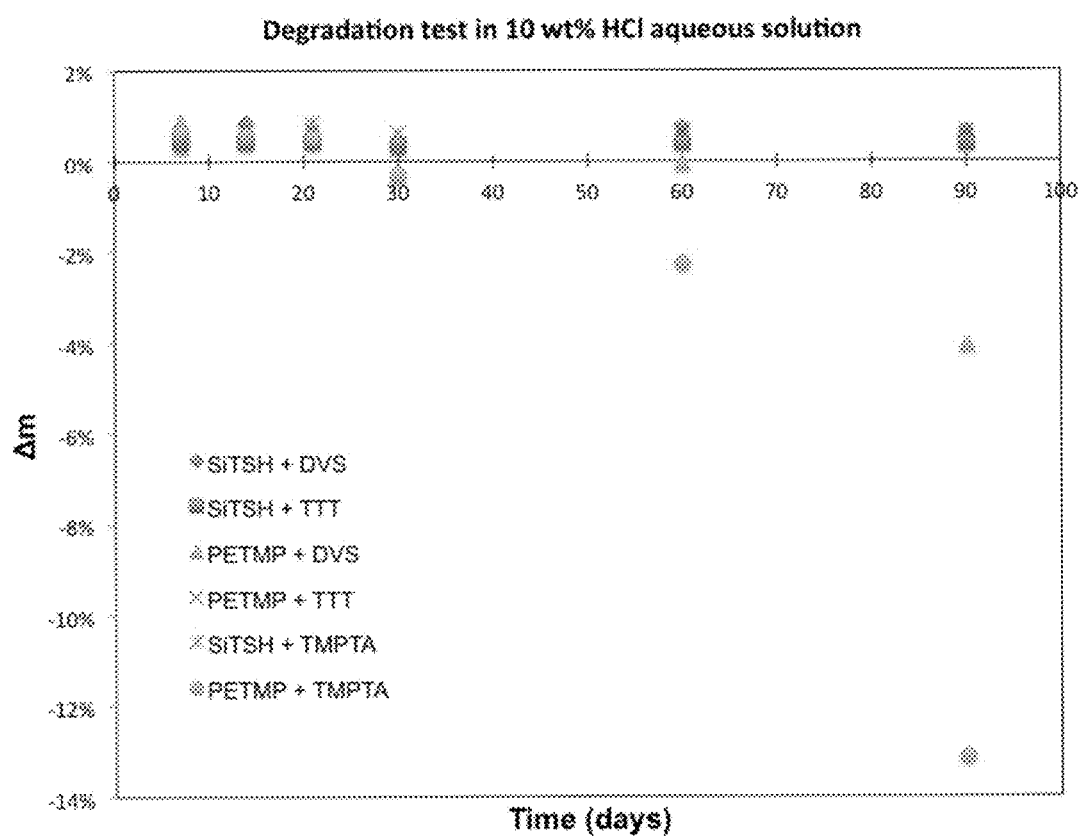
FIG. 17 is a graph that illustrates degradation behavior in 10% HCl aqueous solution over 90 day period.
Figure 18:
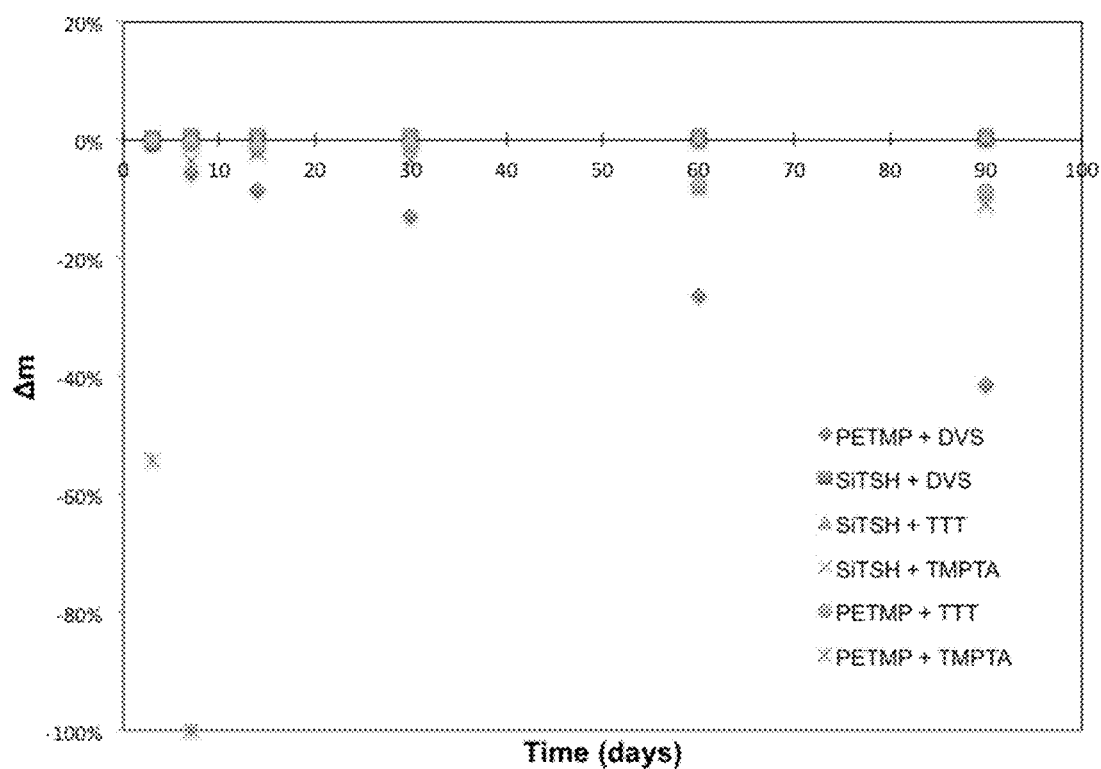
FIG. 18 is a graph that illustrates degradation behavior in 10% NaOH aqueous solution over 90 day period.

To assess the solvent resistance and hydrolytic stability of the networks with varied ester levels, the samples were immersed in acidic and basic solutions for 90 days (Table 6, FIGS. 17-18). As summarized in Table 6, and also in Tables 8-9, only ester-free thiol formulations exhibited less than 1% mass change regardless of the environment type. The more ester groups present in the network, the higher the mass loss observed, especially in basic solutions. The most ester-rich PETMP/TMPTA system degraded completely after less than one week in concentrated basic solvent, and had the highest mass loss in acidic conditions after 90 days. Further, lowering the ester content decelerated the hydrolysis rate as the differences in solvent uptake become less pronounced. Also apparent was the higher hydrophilicity of the DVS containing networks, which absorbed more water, facilitating faster degradation of the ester-containing networks. Plots showing the specimen' mass change (Δm) over time are found in the Supporting Information (FIGS. 17-18, Tables 8-9).

Figure 16:
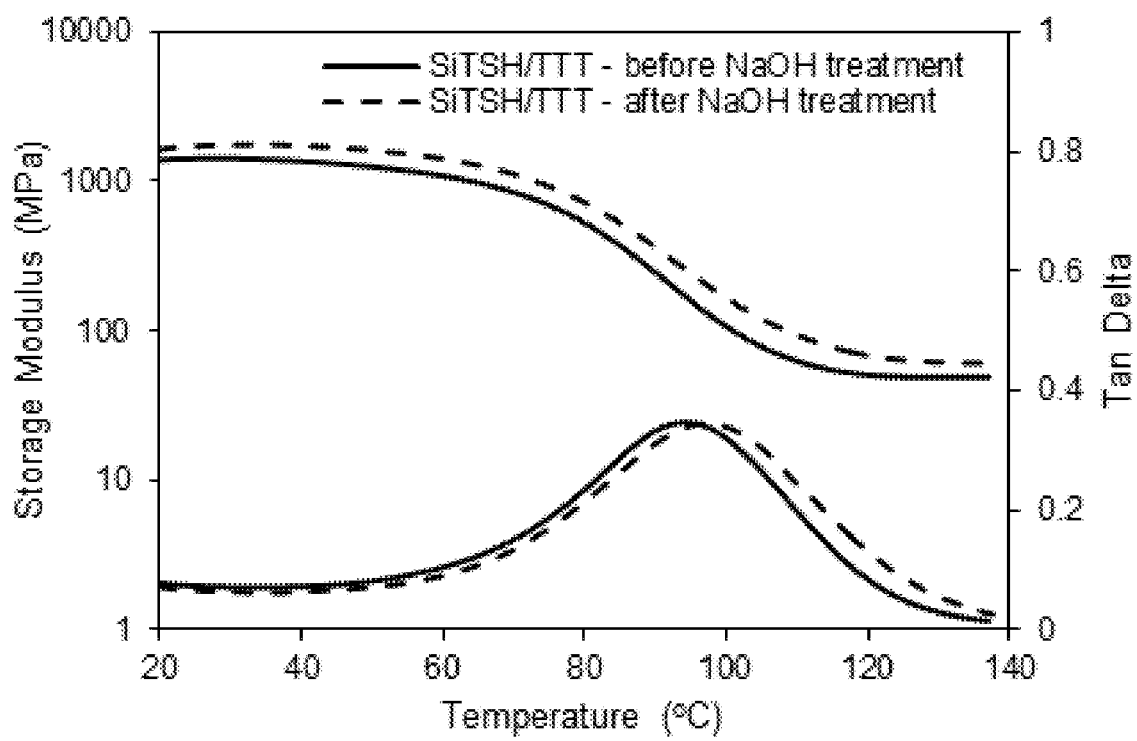
FIG. 16 is a graph illustrating dynamic mechanical analysis of the SiTSH/TTT ester-free system, before (solid line), and after (dashed line) base treatment (20 wt % aqueous NaOH) at boiling conditions for one hour. No change in the mechanical response was detected before and after base treatment.

To push the ester-free samples to their limit, the SiTSH/TTT composition was immersed in 20% boiling NaOH aqueous solution for one hour and afterwards tested the sample in DMA (FIG. 16). Upon comparison of the samples before and after the NaOH treatment, no marked difference between the runs was observed. This behavior indicates that the material may be used in all applications where the corrosive base effects have to be prevented. Decreased water uptake/swelling is also of significance for many other coating, lithography and dental resin applications. In certain embodiments, swelling in water (or other aqueous solutions) decreases the mechanical performance by lowering the modulus and strength. In other embodiments, reducing hydrolytic degradation is of biological significance for thiol-ene materials since the leachable components may be eliminated and the overall biocompatibility improved.

TABLE 6

Summary of the mechanical, and solvent resistance properties of the six tested systems. Maximal conversions after thermal annealing are also included. 10% aqueous HCl and 10% aqueous NaOH were selected as the media for hydrolytic tests. ± at each value stands for sample mass gain/loss. Brackets show standard deviations values.

| | Properties | | | | |
| --- | --- | --- | --- | --- | --- |
| Resin | Ester groups (mol %) | $T_g$ (° C.) | Conv. (%) | wt % Loss/Gain (10 wt % $HCl_{aq}$) | wt % Loss/Gain (10 wt % $NaOH_{aq}$) |
| SiTSH/TTT | 0 | 95 (6) | 84 (2) | +0.4 (0.1) | +0.5 (0.1) |
| PETMP/TTT | 0.49 | 79 (1) | 93 (1) | +0.7 (0.1) | −7.9 (1.5) |
| SiTSH/TMPTA | 0.59 | 35 (3) | 99 (1) | +0.4 (0.1) | −11 (2) |
| PETMP/TMPTA | 0.91 | 21 (1) | 96 (1) | −13 (1) | Degraded after 7 days |
| SiTSH/DVS | 0 | 64 (8) | 99 (1) | +0.7 (0.2) | +0.7 (0.1) |
| PETMP/DVS | 0.55 | 44 (3) | 98 (1) | −4.0 (0.1) | −41 (4) |

The studies reported herein showed that conventional crosslinking step growth systems based on efficient thiol-X reactions can result in glassy materials when the ester functionalities are removed or significantly reduced in content. Uniform network polymers were readily prepared with good conversions, which is one of the attributes of step growth systems. Step-growth polymer networks devoid of ester groups are resistant to corrosive basic or acidic conditions. Ester-free thiol-ene networks were shown to withstand concentrated basic treatment for an extended amount of time without any detrimental effects observed in the thermo-mechanical properties.

TABLE 7

Double bond consumption rates for the tested compositions. $RP_{(max)}$ values were calculated between 10 and 40% double bond conversions, and they are average values of three IR runs.

| Compositions | $RP_{(max)}$ (mmol × s$^{-1}$) | St. Dev. |
| --- | --- | --- |
| SiTSH/DVS | 0.206 | 0.039 |
| PETMP/DVS | 0.038 | 0.004 |
| SiTSH/TMPTA | 0.015 | 0.001 |
| PETMP/TMPTA | 0.002 | 0.001 |
| SiTSH/TTT | 0.072 | 0.002 |
| PETMP/TTT | 0.386 | 0.048 |

TABLE 8

Summary of the solvent resistance properties in 10% aqueous HCl after 30, 60 and 90 days of treatment.

| | Cured Resin Properties | | |
| --- | --- | --- | --- |
| Resin | wt % Loss/Gain (10 wt % HCl) Day 30 | wt % Loss/Gain (10 wt % HCl) Day 60 | wt % Loss/Gain (10 wt % HCl) Day 90 |
| SiTSH/TTT | +0.4 ± 0.1 | +0.4 ± 0.1 | +0.4 ± 0.1 |
| PETMP/TTT | +0.7 ± 0.1 | +0.7 ± 0.1 | +0.7 ± 0.1 |
| SiTSH/TMPTA | +0.4 ± 0.1 | +0.5 ± 0.1 | +0.4 ± 0.1 |
| PETMP/TMPTA | +0.5 ± 0.3 | −2.2 ± 0.1 | −13. ± 1 |
| SiTSH/DVS | +0.6 ± 0.2 | +0.7 ± 0.2 | +0.7 ± 0.2 |
| PETMP/DVS | +0.9 ± 0.1 | −0.1 ± 0.1 | −4.0 ± 0.1 |

TABLE 9

Summary of the solvent resistance properties in 10% aqueous NaOH after 30, 60 and 90 days of treatment.

| | Cured Resin Properties | | |
| --- | --- | --- | --- |
| Resin | wt % Loss/Gain (10 wt % NaOH) Day 30 | wt % Loss/Gain (10 wt % NaOH) Day 60 | wt % Loss/Gain (10 wt % NaOH) Day 90 |
| SiTSH/TTT | +0.3 ± 0.1 | +0.2 ± 0.1 | +0.5 ± 0.1 |
| PETMP/TTT | −1.0 ± 0.1 | −3.6 ± 0.6 | −7.9 ± 1.5 |
| SiTSH/TMPTA | −3.3 ± 0.6 | −7.9 ± 0.7 | −11 ± 2 |
| PETMP/TMPTA | Degraded after 7 days | — | — |
| SiTSH/DVS | +0.6 ± 0.2 | +0.5 ± 0.3 | +0.7 ± 0.1 |
| PETMP/DVS | −12.9 ± 0.1 | −26 ± 1 | −41 ± 4 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising one or more multifunctional vinyl sulfone monomers, one or more multifunctional thiol monomers, and at least one isocyanate monomer, wherein (i) at least one multifunctional thiol monomer is trifunctional, tetrafunctional, pentafunctional or hexafunctional as to the thiol group, or (ii) at least one vinyl sulfone monomer is trifunctional, tetrafunctional, pentafunctional or hexafunctional as to the vinyl sulfone group;

wherein the one or more multifunctional vinyl sulfone monomers, the one or more multifunctional thiol monomers and the at least one isocyanate monomer are devoid of ester functionalities;

wherein the at least one isocyanate monomer is selected from the group consisting of a monofunctional isocyanate, a polyfunctional isocyanate, and mixtures thereof;

wherein (i) the thiol equivalent concentration is approximately equal to the sum of the vinyl sulfone equivalent and the isocyanate equivalent concentrations, or (ii) the thiol equivalent, vinyl sulfone equivalent and isocyanate equivalent concentrations are selected such that, upon polymerization of the composition, at least 80% polymerization of the thiol monomer or vinyl sulfone monomer is observed; and wherein, once polymerized, the polymerized composition comprises a crosslinked polymeric network.

2. The composition of claim 1, wherein the monomers in the composition are unpolymerized or at least partially polymerized.

3. The composition of claim 1, further comprising at least one catalyst selected from the group consisting of a base, a nucleophile, a photolabile base, a photolabile nucleophile, and mixtures thereof.

4. The composition of claim 3, wherein the composition undergoes at least partial polymerization when the catalyst is photocleaved.

5. A composition comprising one or more multifunctional vinyl sulfone monomers, one or more multifunctional thiol monomers, and optionally an isocyanate monomer, wherein the one or more multifunctional vinyl sulfone monomers, the one or more multifunctional thiol monomers and the optional isocyanate monomer are devoid of ester functionalities;

wherein, once polymerized, the polymerized composition comprises a crosslinked polymeric network;

wherein at least one vinyl sulfone monomer is selected from the group consisting of divinyl sulfone,

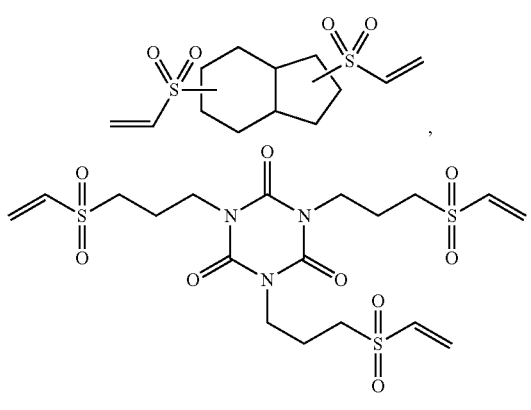

-continued

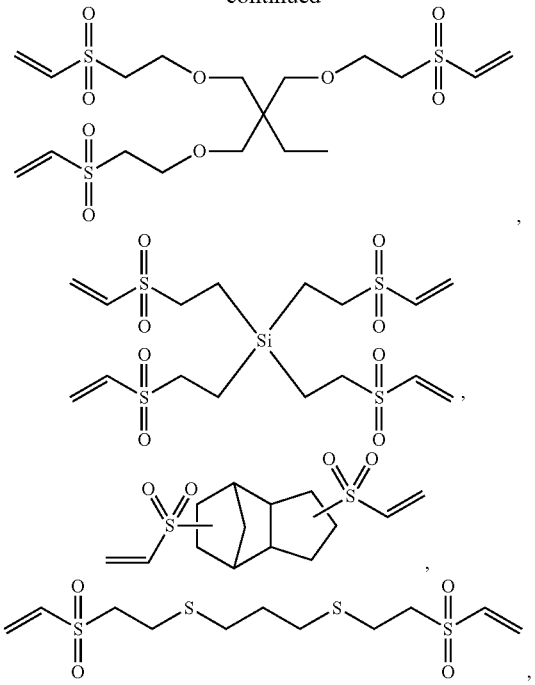

and any combinations thereof; and, wherein at least one thiol monomer is selected from the group consisting of 2,5-dimercaptomethyl-1,4-dithiane, 2,3-dimercapto-1-propanol, 2-mercapto-ethyl sulfide, 2,3-(dimercaptoethylthio)-1-mercaptopropane, 1,2,3-trimercaptopropane, 1,6-hexanedithiol, 1,2-benzenedithiol, 1,3-benzenedithiol, isophorone diurethane thiol,

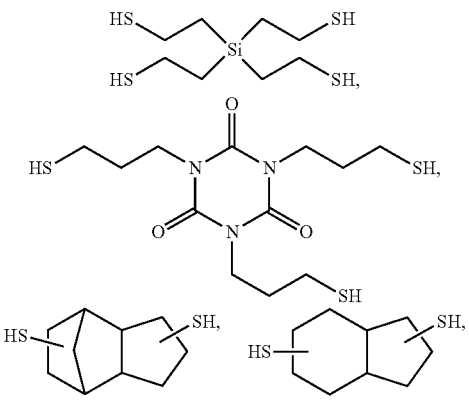

and any combinations thereof.

6. The composition of claim 1, wherein the one or more thiol monomers are independently difunctional, trifunctional, tetrafunctional, pentafunctional or hexafunctional as to the thiol group, and wherein the one or more vinyl sulfone monomers are independently difunctional, trifunctional, tetrafunctional, pentafunctional or hexafunctional as to the vinyl sulfone group.

7. A method of photoinducing a thiol-Michael addition reaction, the method comprising photo-irradiating a composition comprising a thiol monomer, a Michael acceptor monomer, at least one isocyanate monomer, and at least one catalyst selected from the group consisting of a photolabile base, a photolabile nucleophile, and mixtures thereof;
wherein the at least one isocyanate monomers is selected from the group consisting of a monofunctional isocyanate, a polyfunctional isocyanate, and mixtures thereof; and
wherein (i) the thiol equivalent concentration is approximately equal to the sum of the vinyl sulfone equivalent and the isocyanate equivalent concentrations, or (ii) the thiol equivalent vinyl sulfone equivalent and isocyanate equivalent concentrations are selected such that upon polymerization of the composition, at least 80% polymerization of the thiol monomer or vinyl sulfone monomer is observed.

8. The method of claim 7, wherein the photolabile base or photolabile nucleophile comprises a protective group selected from the group consisting of:

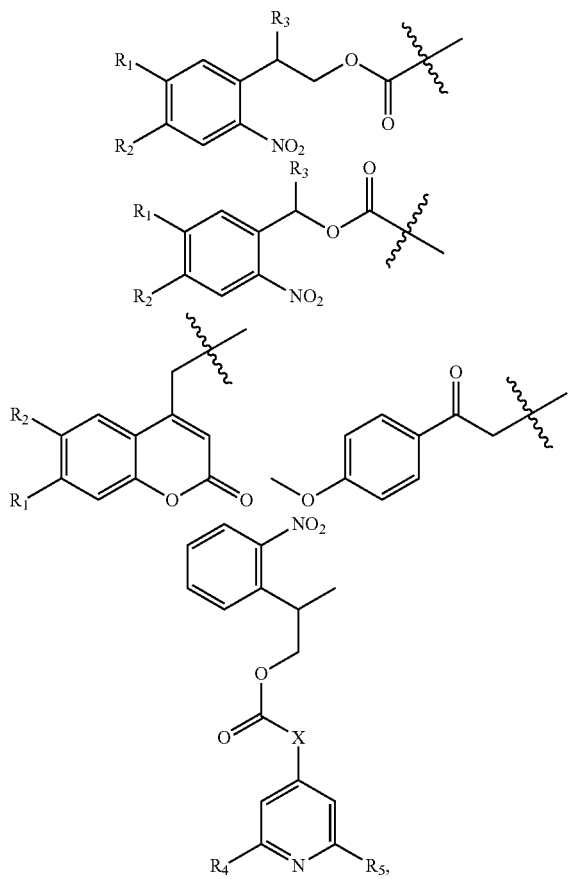

wherein:
each occurrence of $R_1$ and $R_2$ is independently H or $OCH_3$,
each occurrence of $R_3$ is independently H, $CH_3$, $C(=O)$ OH or $C(=O)OCH_3$,
X is NH or O, and
each occurrence of $R_4$ and $R_5$ is independently H or $CH_3$.

9. The method of claim 7, wherein the at least one catalyst comprises a tertiary amine, wherein each substituent on the tertiary amine or phosphine is independently selected from the group consisting of alkyl, substituted alkyl, aryl and substituted aryl.

10. The method of claim 7, wherein the Michael acceptor monomer comprises a (meth)acrylate, maleamide, or vinyl sulfone.

11. The method of claim 7, wherein photo-irradiating the composition promotes at least partial polymerization of the monomers.

12. The method of claim 7, wherein the composition further comprises a filler comprising a thiol- or a vinyl sulfone-functionalized particle.

13. A composition comprising a multifunctional vinyl sulfone monomer, a tetra(2-mercapto)silane (SiTSH) monomer, and optionally an isocyanate monomer, wherein, once polymerized, the polymerized composition forms a cross-linked polymeric network.

14. The composition of claim 13, wherein the monomers in the composition are unpolymerized or at least partially polymerized.

15. The composition of claim 13, wherein the isocyanate monomer is absent; and wherein (i) the thiol equivalent concentration is approximately equal to the vinyl sulfone equivalent concentration, or (ii) the thiol equivalent and vinyl sulfone equivalent concentrations are selected such that, upon polymerization of the composition, at least 80% polymerization of the thiol or vinyl sulfone monomers is observed.

16. The composition of claim 13, wherein the isocyanate is present and is selected from the group consisting of a monofunctional isocyanate, a polyfunctional isocyanate, and mixtures thereof.

17. The composition of claim 16, wherein (i) the thiol equivalent concentration is approximately equal to the sum of the vinyl sulfone equivalent and the isocyanate equivalent concentrations, or (ii) the thiol equivalent, vinyl sulfone equivalent and isocyanate equivalent concentrations are selected such that, upon polymerization of the composition, at least 80% polymerization of the thiol monomer or vinyl sulfone monomer is observed.

18. The composition of claim 13, wherein the composition is essentially free of any other thiol monomer apart from SiTSH.

19. The composition of claim 13, wherein the at least partially polymerized composition is stable to acidic or basic conditions.

20. The composition of claim 13, wherein the monomers are at least partially polymerized by step-growth dispersion click chemistry to form microspheres.

21. The composition of claim 20, wherein the microspheres have an average diameter within a range selected from the group consisting of: from 0.5 µm to 100 µm, from 1 µm to 50 µm, from 0.5 µm to 1 µm; and from 1 µm to 10 µm.

22. The composition of claim 20, wherein the microspheres are near-monodisperse or monodisperse.

23. The composition of claim 20, wherein the microspheres have a glass transition temperature (Tg) in the range of −50° C. to 100° C. or a Tg in the range of −24° C. to 16° C.

24. A method of generating a polymeric material, the method comprising polymerizing at least partially a composition comprising the tetra(2-mercapto)silane (SiTSH) monomer and at least one selected from the group consisting of (a) a Michael acceptor, optionally an isocyanate monomer, and optionally at least one catalyst; (b) an ene monomer, and optionally a polymerization photoinitiator.

25. The method of claim 24, wherein in (a) the at least one catalyst is present and is selected from the group consisting of a base, a nucleophile, a photolabile base, a photolabile nucleophile, and mixtures thereof.

26. The method of claim 24, wherein the polymerized composition comprises microspheres.

* * * * *